United States Patent
Mishima et al.

(10) Patent No.: US 7,252,657 B2
(45) Date of Patent: Aug. 7, 2007

(54) DISPOSABLE WEARING ARTICLE HAVING WASTE-RECEIVING POCKET

(75) Inventors: Yoshitaka Mishima, Kagawa-ken (JP); Kaiyo Nakajima, Kagawa-ken (JP); Kyo Kikuchi, Kagawa-ken (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 0 days.

(21) Appl. No.: 10/983,635

(22) Filed: Nov. 9, 2004

(65) Prior Publication Data

US 2005/0107761 A1    May 19, 2005

(30) Foreign Application Priority Data

Nov. 14, 2003  (JP)  .............................. 2003-385161
Feb. 5, 2004   (JP)  .............................. 2004-029475

(51) Int. Cl.
    *A61F 13/15* (2006.01)
    *A61F 13/20* (2006.01)

(52) U.S. Cl. ........................... 604/385.28; 604/385.27; 604/385.24

(58) Field of Classification Search ......... 604/385.101, 604/385.01, 385.24–385.3
See application file for complete search history.

(56) References Cited

U.S. PATENT DOCUMENTS

| | | | |
|---|---|---|---|
| 4,413,996 A * | 11/1983 | Taylor | ........................ 604/382 |
| 4,501,586 A * | 2/1985 | Holtman | ...................... 604/380 |
| 5,026,363 A * | 6/1991 | Pratt | ...................... 604/385.21 |
| 5,062,840 A * | 11/1991 | Holt et al. | ............. 604/385.19 |
| 5,601,546 A * | 2/1997 | Tanji et al. | ............. 604/385.28 |
| 6,429,351 B1 * | 8/2002 | Guidotti et al. | ............. 604/378 |
| 6,465,712 B1 * | 10/2002 | Matthews et al. | ........... 604/378 |
| 6,869,423 B2 * | 3/2005 | Onishi et al. | ........... 604/385.01 |
| 2002/0013567 A1 * | 1/2002 | Mishima et al. | ....... 604/385.101 |

FOREIGN PATENT DOCUMENTS

| JP | 5-44115 | | 6/1993 |
| JP | 08191857 A | * | 7/1996 |
| JP | 2001-61888 | | 3/2003 |

OTHER PUBLICATIONS

Machine-assisted translation of JP 08-191857 A, accessed Apr. 18, 2006.*

* cited by examiner

*Primary Examiner*—Michele Kidwell
(74) *Attorney, Agent, or Firm*—Lowe, Hauptman & Berner, LLP

(57) ABSTRACT

In a disposable wearing article, and area of a rear waist region in which a core is present is divided into a first area and a second area. The second area is formed in its transversely middle zone with a through-hole extending through the core. A transverse flexural stiffness of the core lying in the second area is lower than a transverse flexural stiffness of the core lying in the crotch region and the first area. Proximal portions of leak-barrier sheets and longitudinal ends of elastic members are in the first area. The first area lies above the crotch region in a thickness direction of the article and the second area forms a barrier and a pocket.

16 Claims, 13 Drawing Sheets

DISPOSABLE WEARING ARTICLE HAVING WASTE-RECEIVING POCKET

RELATED APPLICATIONS

The present application is based on, and claims priority from, Japan Application Serial Number 2003-385161, filed Nov. 14, 2003 and 2004-29475, filed Feb. 5, 2004, the disclosures of which are hereby incorporated by reference herein in their entirety.

BACKGROUND OF THE INVENTION

The present invention relates to a disposable wearing article used for absorption and containment of bodily waste discharged thereon.

In Japanese Unexamined Patent Application Publication No. 2001-61888 (hereinafter referred to as "Citation"), there has already been disclosed a disposable wearing article contoured by front and rear end portions extending in a transverse direction and transversely opposite lateral portions, the front and rear end portions defining therebetween a front waist region, a rear waist region and a crotch region extending between the waist regions. The article comprises a liquid-previous topsheet, a liquid-impervious backsheet, a pair of liquid-impervious leak-barrier sheets including stretchable elastic members extending in the longitudinal direction and contractibly attached thereto so as to bias the leak-barrier sheets to rise up above the topsheet under a contractile force of these elastic members and a liquid-absorbent core interposed between the top- and backsheets so as to extend on the front waist region and the crotch region. The rear waist is divided into a first area put aside toward the rear end portion and a second area put aside toward the crotch region and wherein a stiffness of the second area is lower than those of the first area and the crotch region and proximal portion of the leak-barrier sheets as well as longitudinal ends of the elastic members lie on the first area of the rear waist region.

The first area comprises the top- and backsheets and a band-like waist-surrounding elastic member interposed between these sheets. The proximal portions of the leak-barrier sheets are permanently bonded to the outer surface of the topsheet extending on the first area. In the known article, a contractile force of the elastic members attached to the leak-barrier sheets pulls the first area toward the crotch region so that the first area comes above the crotch region in the thickness direction of the article. Thereupon a difference in level appears between the crotch region and the first area and the second area forms a pocket opening toward the crotch region. Even if bodily waste spreads on the topsheet toward the rear end portion, such bodily waste is received by the pocket and thereby leak of bodily waste beyond the rear end portion can be prevented.

In the case of the article disclosed in Citation, there is an anxiety that the pocket might be collapsed when a body weight of the wearer is exerted on the rear waist region of the article put on the wearer's body and, in consequence, bodily waste might leak out from the pocket and eventually might leak beyond the first area and the rear end portion from the article. The core is not present in the first and second areas, so it is impossible for the first area and the second area forming the pocket to absorb bodily waste. Bodily waste staying in the pocket will readily leak out from the pocket as the pocket is collapsed.

SUMMARY OF THE INVENTION

It is an object of the present invention to provide a disposable wearing article improved so that a collapse-resistant pocket can be formed in the rear waist region, bodily waste can be absorbed even in the barrier as well as in the pocket and leakage of bodily waste beyond the rear end portion can be reliably prevented.

The present invention is directed to a disposable wearing article contoured by front and rear end portions extending in a transverse direction and transversely opposite side portions, the front and rear end portions defining therebetween a front waist region, a rear waist region and a crotch region extending between the waist regions. The article comprises a liquid-previous topsheet, a liquid-impervious backsheet, a pair of liquid-impervious first leak-barrier sheets laid on the transversely opposite side portions so as to extend in a longitudinal direction and a liquid-absorbent core interposed between the top- and backsheets so as to extend between the front and rear end portions. The first leak-barrier sheets respectively comprise proximal portions extending in the longitudinal direction between the front and rear end portions, distal portions extending in the longitudinal direction along the proximal portions and normally biased to rise up above the topsheet and fixed longitudinally opposite end portions laid on the front and rear end portions and collapsed in the transverse direction. Stretchable first elastic members extending in the longitudinal direction are contractibly attached to the distal portions of the first leak-barrier sheets.

The article according to the present invention further comprises an area of the rear waist region in which the core extends being divided into a first area lying on a side of the rear end portion and a second area lying on a side of the crotch region wherein a flexural stiffness of the core is lower in the second area than in the first area and the proximal portions of the first leak-barrier sheets as well as longitudinal end portions of the first elastic members lie in the first area of the rear waist region. The first area is pulled to the crotch region and thereby comes above the crotch region as viewed in a thickness direction of the article and the second area forms at least one of a barrier extending in the thickness direction of the article and a pocket facing the crotch region.

The present invention may include the following preferred embodiments.

The second area is formed in its transversely middle zone with a through-hole extending through the core in the thickness direction. The transversely middle zone of the second area formed with the through-hole contains no core and therefore a transverse flexural stiffness of the core lying in this second area is lower than a transverse flexural stiffness of the core lying in the crotch region and the first area.

The core lying in the transversely opposite side portions of the second area is partially cut off to form a pair of notches which are concave inward as viewed in the transverse direction of the article. The core lying along the transversely opposite side portions of the second area is cut off so as to form a pair of notches in which no core is present and therefore a transverse flexural stiffness of the core lying in the second area is lower than a transverse flexural stiffness of the core lying in the crotch region and the first area.

A basis weight, a density and a thickness dimension of the core are uniform in said crotch region, the first area and the second area.

The article includes a liquid-impervious second leak-barrier sheet comprising a proximal portion lying in the first area of the rear waist region and extending in the transverse direction, a distal portion extending along the proximal portion in the transverse direction from the first area to the second area of the rear waist region and fixed transversely opposite side portions lying on a side of the transversely opposite side portions of the article and collapsed inward as viewed in a longitudinal direction and wherein a stretchable second elastic member extending in the transverse direction is contractibly attached to the distal portion of the second leak-barrier sheet.

The second leak-barrier sheet extends to straddle the pair of first leak-barrier sheets and the distal portion of the second leak-barrier sheet is permanently bonded along the transversely opposite side portions thereof to the distal portions of the first leak-barrier sheets.

A transverse flexural stiffness value of the core lying in the crotch region and the first area is in a range of 9.4 to 28.2 mN as measured by the Gurley's Method and a transverse flexural stiffness value of the core lying in the second area is in a range of 5.5 to 16.5 mN as measured by the Gurley's Method.

The distal portions of the first leak-barrier sheets respectively including the first elastic members exhibit a stretch stress in a range of 0.02 to 0.32 N at 90% stretched state.

In the article according to the present invention, the second area of the rear waist region is partially bent under the contractile force of the first elastic members attached to the first leak-barrier sheets whereby the first area of the rear waist region is pulled toward the crotch region until the first area comes above the crotch region as viewed in the thickness direction of the article so that a difference in level appears between the crotch region and the first area and the second area forms at least one of the barrier extending in the thickness direction of the article and the pocket facing the crotch region. Assumed that the second area forms the barrier, even if bodily waste discharged on the article put on the wearer's body spreads on the topsheet toward the rear end portion, the second area can function to prevent bodily waste from further spreading beyond the first area and leaking out from the article beyond the rear end portion of the article. Assumed that the second area forms the pocket, even if bodily waste discharged on the article put on the wearer's body spreads on the topsheet toward the rear end portion, such bodily waste will be received by the pocket without further spreading beyond the first area and leaking out from the article beyond the rear end portion. In this way, the article according to the present invention ensures that bodily waste is absorbed by the core lying in the first and second areas without any anxiety that bodily waste might stay on the barrier and/or within the pocket and bodily waste might leak out from the pocket.

In the case of the article wherein the second area is formed in its transversely middle zone with a through-hole extending through the core in the thickness direction, a difference in level appears between the transversely opposite side zones and the transversely middle zone of the second area depending on a differential thickness dimension of the core. With such an arrangement, even when a body weight of the wearer is exerted on the rear waist region and thereby the second area is compressed in the thickness direction of the article, the transversely middle zone is prevented by the thickness of the core present in the transversely opposite lateral zones from being collapsed. This is because the transversely opposite side zones in which the core is present are respectively folded upon themselves before the transversely middle zone might be folded upon itself. Even if the pocket is collapsed in the transversely opposite side zones of the second area, there is no possibility that the pocket might be collapsed in the transversely middle zone. Thus the pocket can be kept in the opened state so far as the transversely middle zone is concerned, so it is unlikely that bodily waste might leak out from the pocket and further leak out from the article beyond the rear end portion even when a body weight of the wearer is exerted on the rear waist region. Bodily waste is reliably absorbed by the core lying in the first area and the transversely opposite lateral zones of the second area without staying on the barrier and/or in the pocket.

In the case of the article wherein the core lying in the transversely opposite lateral portions of the second area is partially cut off to form a pair of notches which are concave inward as viewed in the transverse direction of the article, a difference in level depending on a differential thickness dimension of the core appears between the middle zone and the side zones. With such an arrangement, even when a body weight of the wearer is exerted on the rear waist region and thereby the second area is compressed in the thickness direction of the article, the transversely lateral zones is prevented by the thickness of the core which is present in the transversely middle zone from being collapsed. This is because the transversely middle zone containing the core is folded upon itself before the transversely opposite side zones of the second area might be folded upon each other. Even if the pocket is collapsed in the transversely middle zone of the second area, there is no possibility that the pocket might be collapsed in the transversely opposite lateral zones. Thus the pocket can be kept in the opened state so far as the transversely opposite lateral zones are concerned, so it is unlikely that bodily waste might leak out from the pocket and further leak out from the article beyond the rear end portion even when a body weight of the wearer is exerted on the rear waist region. Bodily waste is reliably absorbed by the core lying in the first area and the transversely middle zone of the second area without staying on the barrier and/or within the pocket.

In the case of the article wherein a basis weight, a density and a thickness dimension of the core are uniform in the crotch region, the first area and the second area and wherein the core is formed with the through-hole or the notches, it is unlikely that the core lying in the first area and the crotch region might be irregularly bent under a contractile force of the first elastic members attached to the first leak-barrier sheets. Consequently, the core lying in the second area can be reliably bent and thereby the first area can be reliably pulled toward the crotch region. In addition, there is no anxiety that the core might become locally bulky and locally increased stiffness of the core might create a feeling of discomfort against the wearer.

In the case of the article wherein the article includes a liquid-impervious second leak-barrier sheet lying in the rear waist region and extending in the transverse direction, the distal portion of this second leak-barrier sheet forms the barrier against bodily waste adapted to prevent bodily waste discharged on the article put on the wearer's body from leaking out from the article beyond the rear end portion even if bodily waste spreads beyond the barrier formed by the second area to the first area.

In the case of the article wherein the second leak-barrier sheet extends to straddle the pair of first leak-barrier sheets and the free portion of the second leak-barrier sheet is permanently bonded along the transversely opposite side portions thereof to the distal portions of the first leak-barrier sheets, the distal portion of the second leak-barrier sheet is spaced apart upward from the topsheet as the distal portions of the first leak-barrier sheets rise up above the topsheet. In this way, the distal portion of this second leak-barrier sheet reliably functions as the barrier adapted to prevent bodily waste from leaking out from the article beyond the rear end portion.

In the case of the article wherein a transverse flexural stiffness value of the core lying in the crotch region and the first area is in a range of 9.4 to 28.2 mN as measured by the Gurley's Method and a transverse flexural stiffness value of the core lying in the second area is in a range of 5.5 to 16.5 mN as measured by the Gurley's Method, the contractile force of the first elastic members causes the core to be bent only in the second area without being accompanied with irregular bending of the core in the first area as well as in the crotch region. As a result, the first area can be reliably pulled toward the crotch region and the barriers and/or the pocket can be reliably formed.

In the case of the article wherein the distal portions of the first leak-barrier sheets respectively including the first elastic members exhibit a stretch stress in a range of 0.02 to 0.32 N at 90% stretched state, the contractile force of the first elastic members are sufficiently exerted on the first area to pull this first area toward the crotch region so that the second area can reliably form the barriers and/or the pocket.

PREFERRED EMBODIMENTS OF THE INVENTION

Details of a disposable wearing article according to the present invention will be more fully understood from the description given hereunder with reference to the accompanying drawings.

Figure 1:
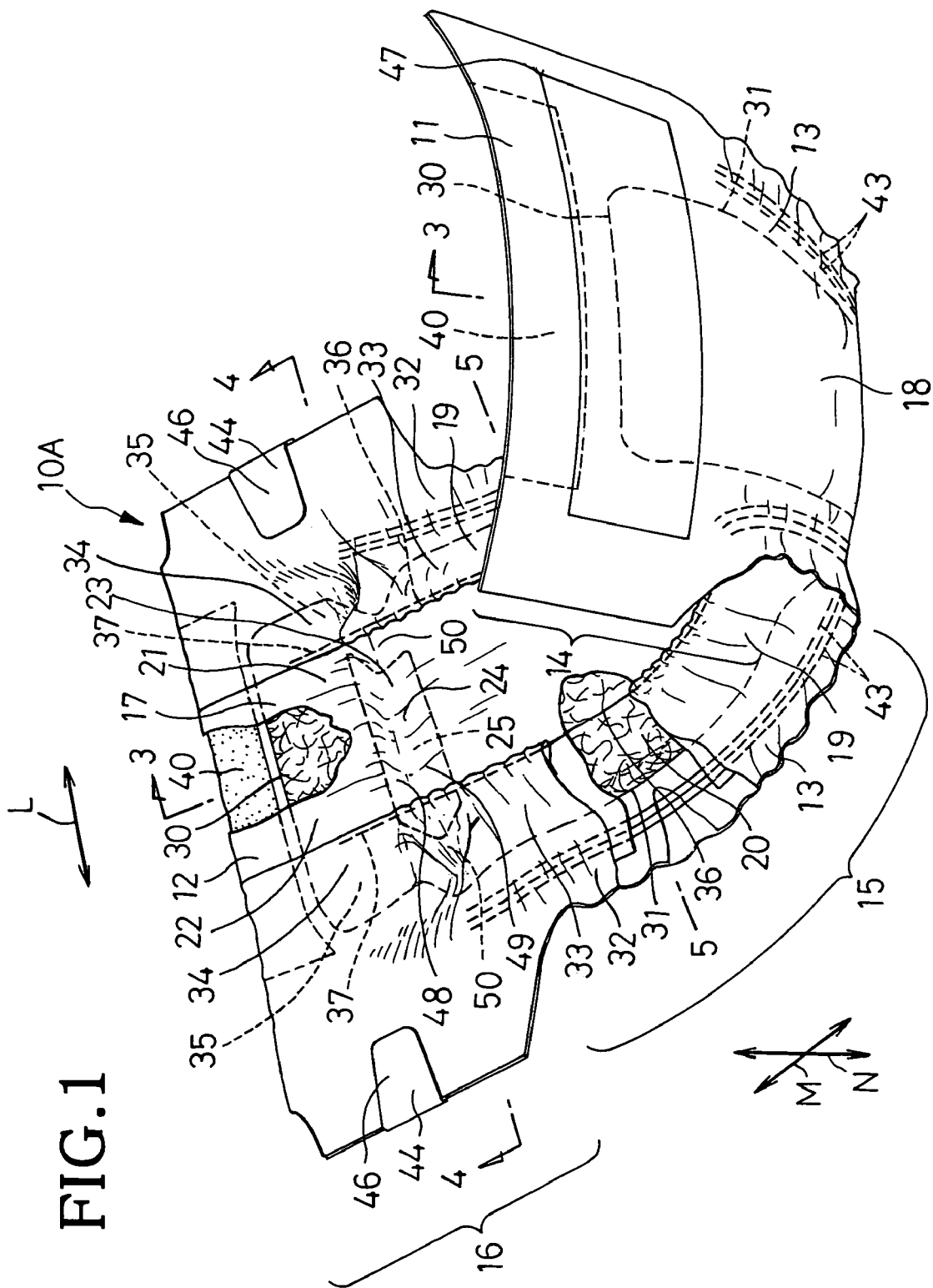
FIG. 1 is a partially cutaway perspective view showing a disposable diaper as a typical embodiment of the invention.
Figure 2:
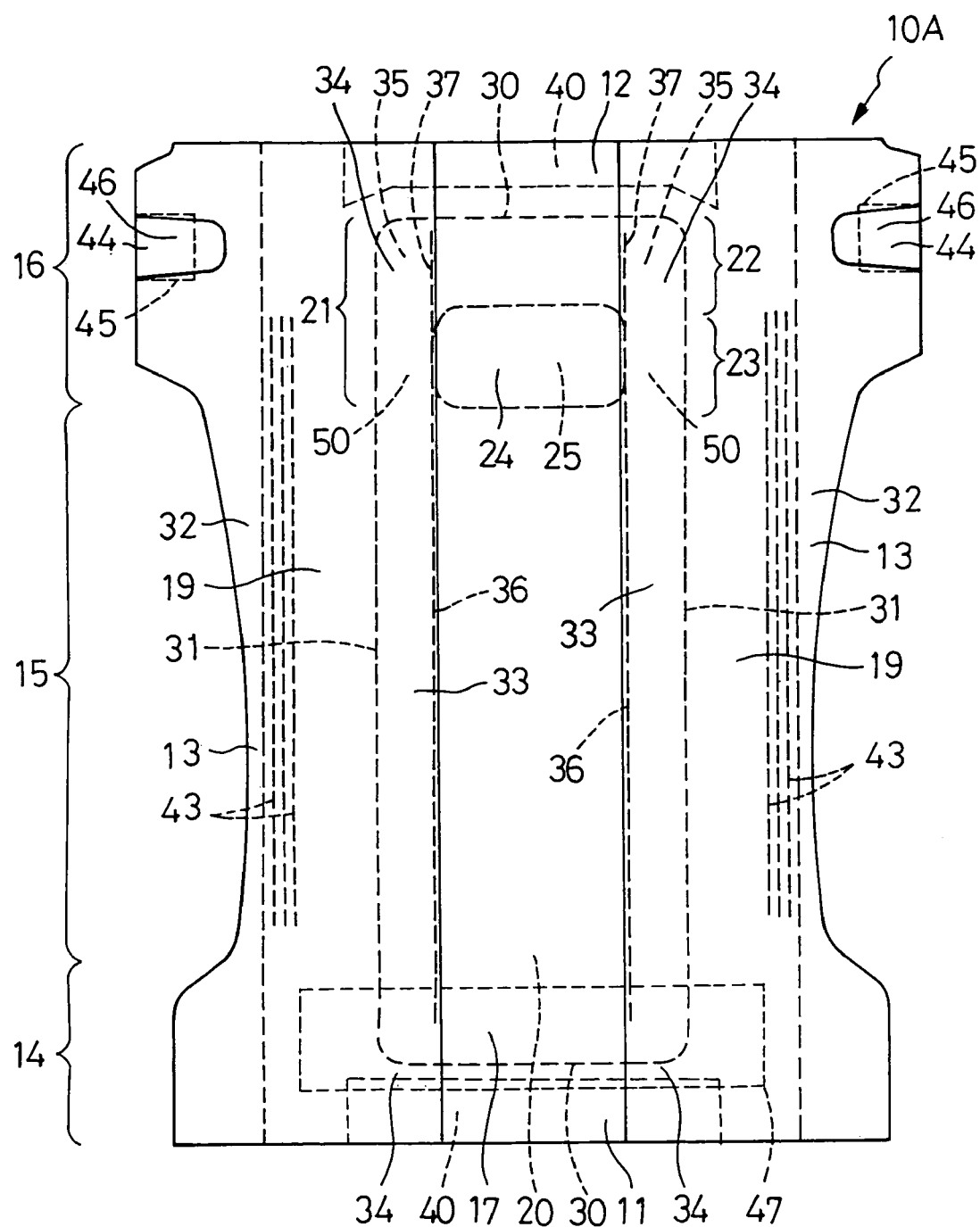
FIG. 2 is a plan view showing the article of FIG. 1 as seen from the side of the topsheet.
Figure 3:
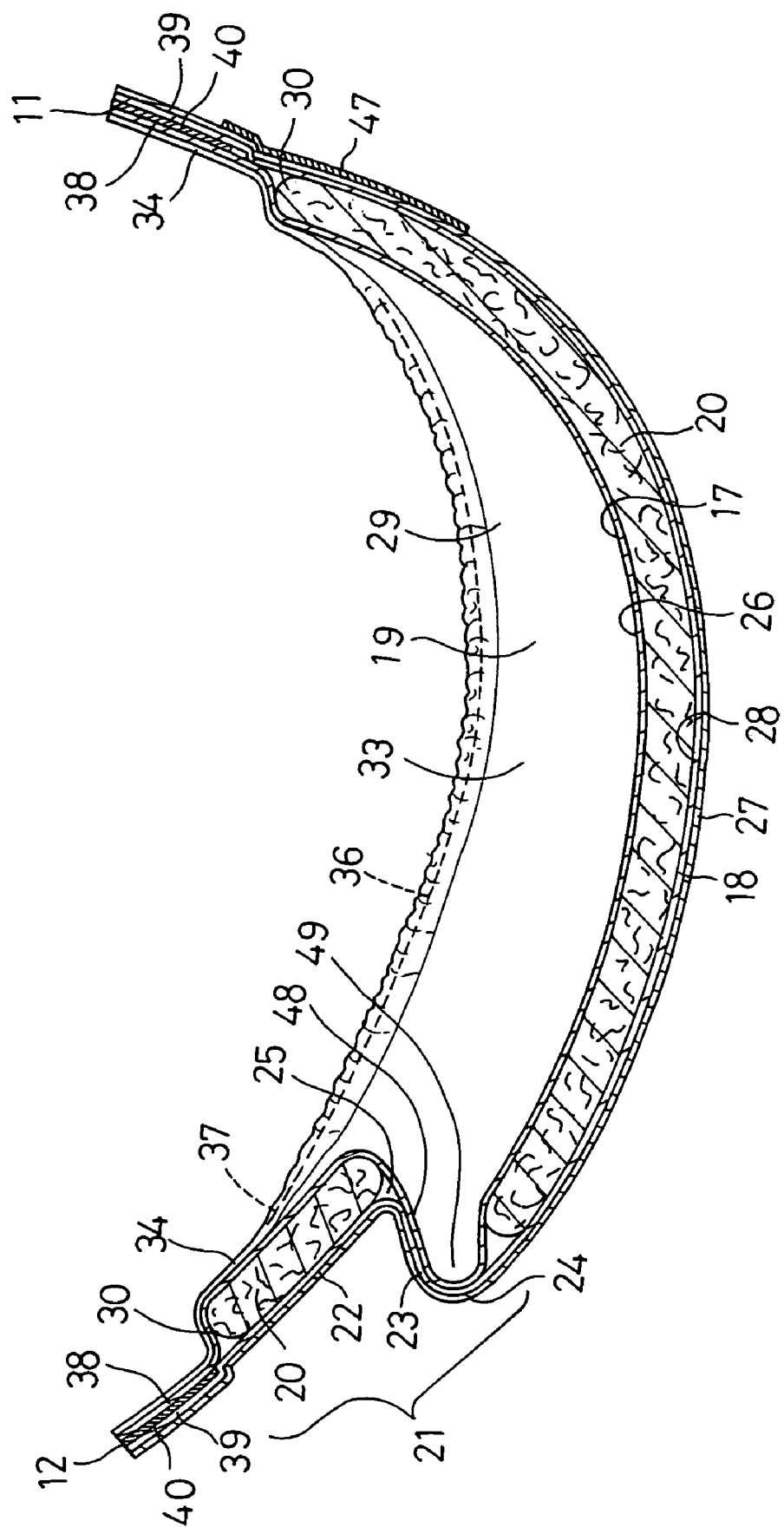
FIG. 3 is a sectional view taken along the line 3-3 in FIG. 1.
Figure 4:
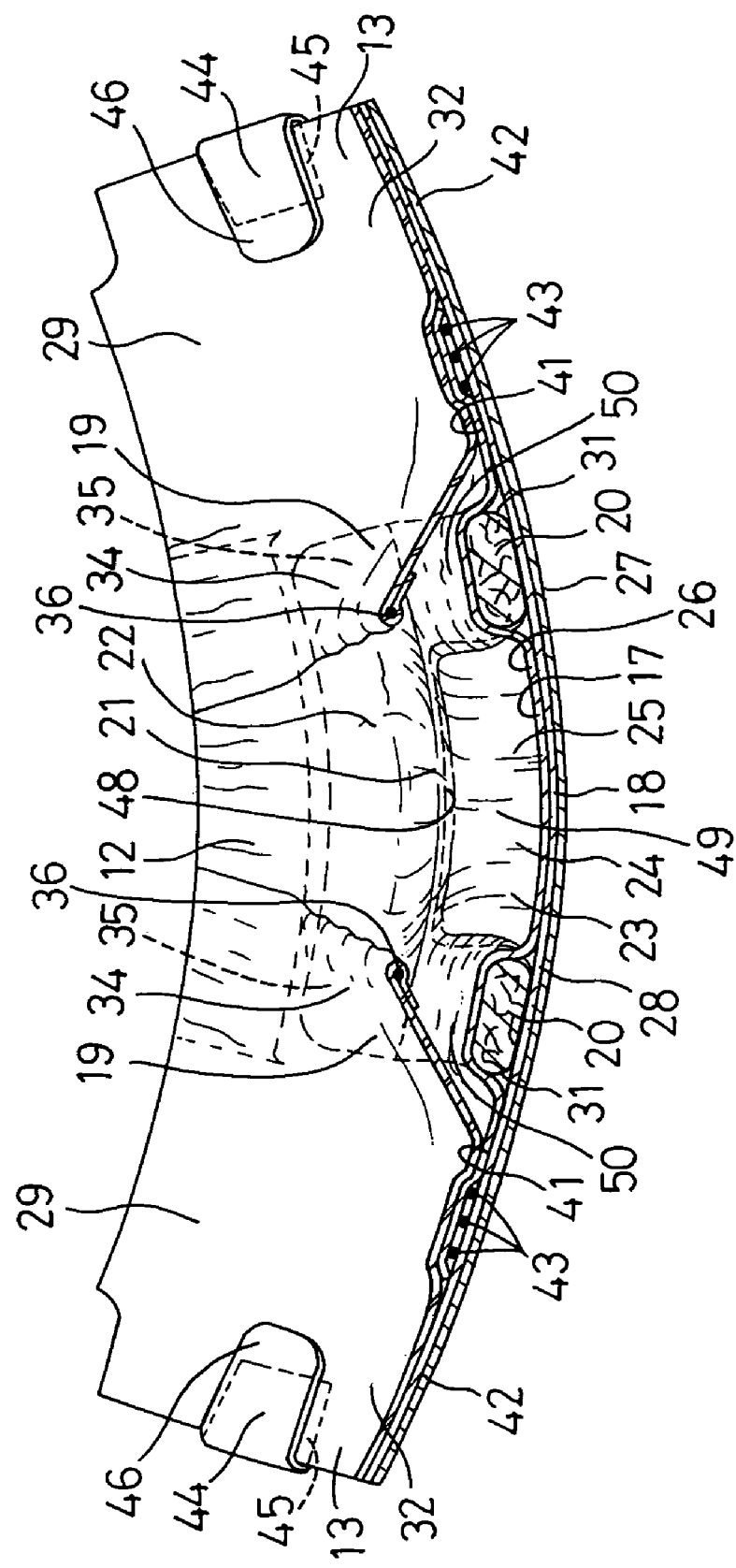
FIG. 4 is a sectional view taken along the line 4-4 in FIG. 1.
Figure 5:
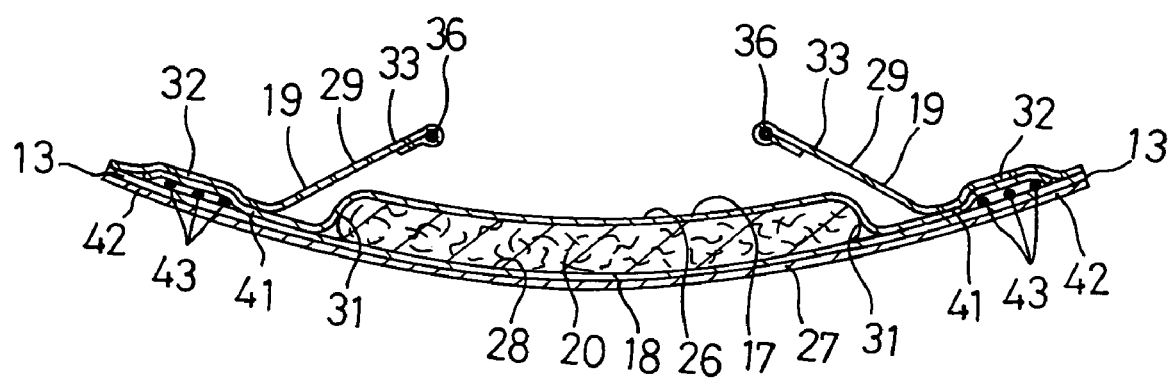
FIG. 5 is a sectional view taken along the line 5-5 in FIG. 1.

FIG. 1 is a partially cutaway perspective view showing a disposable wearing article 10A as a typical embodiment of the invention and FIG. 2 is a plan view showing the article 10 of FIG. 1 as seen from the side of the topsheet 17. In FIG. 1, a transverse direction is indicated by an arrow L, a longitudinal direction is indicated by an arrow M and a thickness direction is indicated by an arrow N. FIG. 2 shows the article 10A as has been developed in the longitudinal direction as well as in the transverse direction against a contractile force of elastic members 36, 40, 43. FIG. 3 is a sectional view taken along the line 3-3 in FIG. 1, FIG. 4 is is a sectional view taken along the line 4-4 in FIG. 1 and FIG. 5 is a sectional view taken along the line 5-5 in FIG. 1.

The article 10A is contoured by front and rear end portions 11, 12 extending in parallel to each other in the transverse direction and a pair of transversely opposite side portions 13 extending in the longitudinal direction. Between the front and rear end portions 11, 12, the article 10A has, as viewed in the longitudinal direction, a front waist region 14, a rear waist region 16 and a crotch region 15 extending between these waist regions 14, 16. The article 10A comprises a liquid-previous topsheet 17 facing the wearer's skin, a liquid-impervious backsheet 18 facing away from the wearer's skin, a pair of liquid-impervious leak-barrier sheets 19 lying on the side portions 13 and extending in the longitudinal direction, and a liquid-absorbent core 20 interposed between the top- and backsheets 17, 18 and bonded to respective inner surfaces of these sheets 17, 18. The core 20 extends continuously in the front and rear waist regions 14, 16 and the crotch region 15. In the crotch region 15, the transversely opposite side portions 13 curve inward as viewed in the transverse direction of the article 10A so as to describe circular arcs. Thus the article 10A has a generally hourglass-like planar shape.

An area 21 of the rear waist region 16 in which the core 20 is present is divided into a first area 22 put aside toward the rear end portion 12 and a second area 23 put aside toward the crotch region 15. The second area 23 is formed in its transversely middle zone 24 with a through-hole 25 extending through the core 20 in its thickness direction. In a range defined by the through-hole 25, the top- and backsheets 17, 18 are put flat together and have respective inner surfaces permanently bonded to each other.

The topsheet 17 is formed from a hydrophilic fibrous nonwoven fabric 26. The backsheet 18 is formed from a composite sheet consisting of a breathable liquid-impervious plastic film 28 and a hydrophobic fibrous nonwoven fabric 27 laminated one upon another. The leak-barrier sheets 19 are formed from a repellent treated hydrophobic fibrous nonwoven fabric 29.

The core 20 is contoured by longitudinally opposite ends 30 extending in the transverse direction and transversely opposite side edges 31 extending in the longitudinal direction. The core 20 comprises a mixture of particulate or fibrous super-absorbent polymer and fluff pulp or a mixture of particulate or fibrous super-absorbent polymers, fluff pulp fibers and thermoplastic synthetic resin fibers, in any case, compressed to a desired thickness. Therefore, the core 20 has a stiffness higher than those of top- and backsheets 17, 18 as well as of the leak-barrier sheets 19. Preferably, the core 20 is entirely wrapped with a tissue paper (not shown) in order to prevent the core 20 from getting out of its initial shape.

Basis weight and density as well as thickness dimension of the core 20 are uniform in the crotch region 15 and the first and second areas 22, 23. A transverse dimension of the core 20 in the second area 23 (inclusive of the through-hole 25) is the same as a transverse dimension of the core 20 in the crotch region 15 as well as in the first area 22. The core 20 preferably has a thickness dimension in a range of 1 to 10 mm. In spite of the fact that the basis weight and the density as well as the thickness dimension of the core 20 are uniform in the crotch region 15 and the first and second areas 22, 23, the core 20 has a transverse flexural stiffness lower in the second area 23 than in the crotch region 15 and the first area 22. This is because the second area 23 is formed in its transversely middle zone 24 with the through-hole 25 in which the core 20 is absent.

The leak-barrier sheets 19 face the wearer's skin and are laid on the outer surface of the topsheet 17. The leak-barrier sheets 19 respectively comprise proximal portions 32 lying on the transversely opposite side portions 13 and extending in the longitudinal direction, distal portions 33 extending in the longitudinal direction along the proximal portions 32 and normally biased to rise up above the topsheet 17, and fixed longitudinally opposite end portions 34 lying on the front and rear end portions 11, 12 and collapsed inward as viewed in the transverse direction of the article 10A. The proximal portions 32 and the distal portions 33 extend between the front and rear end portions 11, 12 of the article 10A. The end portions 34 lying on the side of the rear waist region 16 are respectively laid not only on the rear end portion 12 but also on transversely opposite side portions 35 of the first area 22.

Stretchable first elastic members 36 extending in the longitudinal direction are contractibly attached to the distal portions 33 in the vicinity of respective upper ends thereof. The elastic members 36 are stretched at a predetermined ratio in the longitudinal direction and permanently bonded in such a stretched state to the distal portions 33. Longitudinally ends 37 of the elastic members 36 extending into the rear waist region 16 extend beyond the second area 23 to the transversely opposite side portions 35 of the first area 22. The elastic members 36 contract as the article 10A curves in the longitudinal direction with the topsheet 17 inside. Thereupon the distal portions 33 shrink in the longitudinal direction and rise up above the topsheet 17 under a contractile force of the elastic members 36. As will be seen in FIG. 1, the distal portions 33 of the leak-barrier sheets 19 rise up above the topsheet 17 and form barriers against bodily waste discharged onto the article 10A.

The front and rear end portions 11, 12 comprise respective end portions 38, 39 of the top- and backsheets 17, 18 extending outward in the longitudinal direction beyond the longitudinally opposite ends 30 of the core 20 and the end portions 34 of the respective leak-barrier sheets 19. Along the front and rear end portions 11, 12, the end portions 38, 39 of the top- and backsheets 17, 18 and the end portions 34 of the leak-barrier sheets 19 are put flat together wherein the respective inner surfaces of the top- and backsheets 17, 18 are permanently bonded to each other and the outer surface of the topsheet 17 is permanently bonded to the inner surfaces of the leak-barrier sheets 19. In the rear waist region 16, the end portions 34 of the leak-barrier sheets 19 have respective inner surfaces thereof are permanently bonded to the outer surface of the topsheet 17 in the vicinity of the transversely opposite side portions 35. Band-like waist-surrounding elastic members 40 extending in the transverse direction outside the longitudinally opposite ends 30 are contractibly attached to the front and rear end portions 11, 12. The waist-surrounding elastic members 40 are interposed between the end portions 38 of the topsheet 17 and the end portions 39 of the backsheet 18 and permanently bonded to the respective inner surfaces of these sheets 17, 18 while the elastic members 40 are stretched at a predetermined ratio in the transverse direction.

The transversely opposite side portions 13 comprise the side portions 41, 42 of the top- and backsheets 17, 18 extending outward in the transverse direction beyond the side edges 31 of the core 20 and the proximal portions 32 of the respective leak-barrier sheets 19. Along the side portions 13, the side portions 41 of the topsheet 17 extend outward in the transverse direction slightly beyond the side edges 31 of the core 20 and the side portions 42 of the backsheet 18 as well as the proximal portions 32 of the leak-barrier sheets 19 extend further outward in the transverse direction beyond the side portions 41 of the topsheet 17. Along the transversely opposite side portions 13, the side portions 41, 42 of the top- and backsheets 17, 18 are put flat together with the proximal portions 32 of the leak-barrier sheets 19, and the inner surfaces of the top- and backsheets 17, 18 are permanently bonded together and the inner/outer surfaces of the top- and backsheets 17, 18, respectively, and the inner surfaces of the respective leak-barrier sheets 19 are permanently bonded together. A plurality of leg-surrounding elastic members 43 lying outside the side edges 31 of the core 20 as viewed in the transverse direction and extending in the longitudinal direction are contractibly attached to the side portions 13. These leg-surrounding elastic members 43 are interposed between the side portions 41 of the topsheet 17 and the side portions 42 of the backsheet 18 and permanently bonded to the inner surfaces of the sheets 17, 18 while the elastic members 43 are stretched in the longitudinal direction at a predetermined ratio.

Flexible tape fasteners 44 made of a fibrous nonwoven fabric are respectively attached to the side portions 13 of the rear waist region 16. Each of the tape fasteners 44 has a proximal end portion 45 extending in the transverse direction and a distal end portion 46. The proximal end portion 45 is interposed between the side portion 42 of the backsheet 18 and the proximal portion 32 of the leak-barrier sheet 19 and permanently bonded to the respective inner surfaces of the sheets 18, 19. The distal end portion 46 is provided with a hook member (not shown). The distal end portions 46 are folded inward in the transverse direction of the article 10A and temporarily fixed to the proximal portions 32 of the leak-barrier sheets 19 by means of the hook members. It is possible to replace the hook members 64 provided on the respective distal end portions 63 by pressure-sensitive adhesive protected by a release paper.

A flexible target tape strip 47 is attached to the front waist region 14 so that the distal end portions 46 of the respective tape fasteners 44 may be detachably anchored on this target tape strip 47. The target tape strip 47 has a rectangular shape which is relatively long in the transverse direction, and comprises a plastic film and a loop member (not shown) attached to the film. The film constituting the target tape strip 47 is permanently bonded to the outer surface of the backsheet 18. In the case of the tape fastener 44 having the distal end portion 46 coated with pressure-sensitive adhesive, a plastic film may be used as the target tape strip 47 provided with no loop member thereon.

The article 10A may be put on the wearer's body by folding the side portions 13 of the rear waist region 16 onto the outer side of the side portions 13 of the front waist region 14 and then anchoring the distal end portions 46 of the respective tape fasteners 44 on the target tape strip 47 to connect the front and rear waist regions 14, 16 to each other. Upon connection of the front and rear waist regions 14, 16, the article 10A is formed with a waist-hole and a pair of leg-holes (not shown).

The second area 23 of the rear waist region 16 is partially folded under a contractile force of the elastic members 36 attached to the leak-barrier sheets 19 and the first area 22 is pulled toward the crotch region 15 so that the first area 22 comes above the crotch region 15 in the thickness direction of the article 10A. A difference in level appears between the crotch region 15 and the first area 22 in the thickness direction with interposition of the second area 23 which forms, in turn, a pocket 49 defined between a barrier 48 extending in the thickness direction of the article 10A and the crotch region 15.

Even if bodily waste discharged on the article put on the wearer's body spreads on the topsheet 17 toward the rear end portion 12, further spreading of bodily waste is prevented by the barrier 48 and it is unlikely that bodily waste might leak out from the article 10A beyond the rear end portion 12. The second area 23 forms not only the barrier 48 but also the pocket 49 so that bodily waste flowing toward the rear end portion 12 is received by the pocket 49. In this way, there is no anxiety that bodily waste might leak out beyond the rear end portion 12.

The second area 23 of the article 10A is formed in the transversely middle zone 24 with the through-hole 25 extending through the core 20 in its thickness direction and a difference in level depending on the thickness dimension of the core 20 appears between the middle zone 24 and the side zones 50. With such an arrangement, even when a body weight of the wearer is exerted on the rear waist region 16 and thereby the second area 23 is compressed in the thickness direction of the article 10A, the transversely middle zone 24 is prevented by the thickness of the core 20 present in the side zones 50 from being collapsed. This is because the side zones 50 in which the core 20 is present are respectively folded upon themselves before the transversely middle zone 24 might be folded upon itself. Even if the pocket 49 is collapsed in the transversely opposite side zones 50 of the second area 23, there is no possibility that the pocket 49 might be collapsed in the transversely middle zone 24. Thus the pocket 49 can be kept in the opened state so far as the transversely middle zone 24 is concerned, so it is unlikely that bodily waste might leak out from the pocket 49 and further leak out from the article 10A beyond the rear end portion 12 even when a body weight of the wearer is exerted on the rear waist region 16. Bodily waste is reliably absorbed by the core 20 lying in the first area 22 and the transversely opposite side zones 50 of the second area 23 without staying on the barrier 48 and/or in the pocket 49. Bodily waste discharged onto the crotch region 15 and the front waist region 14 is absorbed by the core 20 which is present in these regions 14, 15 through the topsheet 17.

The core 20 in the crotch region 15 and the first area 22 has a transverse flexural stiffness in a range of 9.4 to 28.2 mN and the core 20 which is present in the second area 23 has a transverse flexural stiffness in a range of 5.5 to 16.5 mN. If the flexural stiffness of the core 20 lying in the crotch region 15 and the first area 22 is less than 9.4 mN, the contractile force of the elastic members 36 may result in irregular bending of the crotch region 15 and the first area 22. Such irregular bending causes a gap to be left between the crotch region 15 and the first area 22, on one hand, and the wearer's skin, on the other hand, and makes it impossible for the core 20 lying in the crotch region 15 and first area 22 to absorb bodily waste efficiently. If the flexural stiffness of the core 20 lying in the crotch region 15 and first area 22 exceeds 28.2 mN, the flexural stiffness of these crotch region 15 and first area 22 will excessively increase and a feeling of discomfort against the wearer will be correspondingly created. If the flexural stiffness of the core 20 lying in the second area 23 is less than 5.5 mN, the second area 23 may be irregularly bent under the contractile force of the elastic members 36 and it may be impossible for the second area 23 to form the barrier 48 and the pocket 49. If the flexural stiffness of the core 20 lying in the second area 23 exceeds 16.5 mN, it may be difficult for the core 20 lying in the second area 23 to be bent properly and it may be impossible for the first area 22 to be pulled toward the crotch region 15 under the contractile force of the elastic members 36. Eventually it may be impossible for the second area 23 to form the barrier 48 and the pocket 49. The flexural stiffness of the core 20 lying in the crotch region 15, the first area 22 and the second area 23 was measured by the Gurley Method (JIS L 1096-01-8.20.1) according to the procedures as follow:

(1) The core 20 is taken off from the article 10A and the core 20 lying in the first area 22 is cut out to obtain a first sample, the core 20 lying in the second area 23 is cut out to obtain a second sample and the core lying in the crotch region 15 is cut out to obtain a third sample. These three samples are same in the size, i.e., in a dimension in the longitudinal direction as well as in a dimension in the transverse direction. For measurement of the flexural stiffness, the Gurley's Stiffness Tester was used.

(2) One of longitudinally opposite end portions of the first sample is held by a chuck of the tester and the other end portion is maintained in engagement with a pendulum of the tester and the tester is initialized by loading an auxiliary weight so that the tester scale may point a reading in a range of 3 to 6; the tester is turned on and a scale reading of the moment at which the pivot rod of the pendulum is separated from the first sample is recorded as a first stiffness value. Now the other of longitudinally opposite end portions of the first sample is held by the chuck of the tester and the one of these end portions is maintained in engagement with the pendulum of the tester. The tester is initialized by loading the auxiliary weight so that the tester scale may point a reading in a range of 3 to 6; the tester is turned on and a scale reading of the moment at which the pivot rod of the pendulum is separated from the sample is recorded as a second stiffness value. An average value of these first and second stiffness values obtained in this manner is recorded as the flexural stiffness value in the transverse direction of the core 20 lying in the first area 22.

(3) One of longitudinally opposite end portions of the second sample is held by a chuck of the tester and the other end portion is maintained in engagement with a pendulum of the tester and the tester is initialized by loading an auxiliary weight so that the tester scale may point a reading in a range of 3 to 6; the tester is turned on and a scale reading of the moment at which the pivot rod of the pendulum is separated from the second sample is recorded as a third stiffness value. Now the other of longitudinally opposite end portions of the second sample is held by the chuck of the tester and the one of these end portions is maintained in engagement with the pendulum of the tester. The tester is initialized by loading the auxiliary weight so that the tester scale may point a reading in a range of 3 to 6; the tester is turned on and a scale reading of the moment at which the pivot rod of the pendulum is separated from the sample is recorded as a fourth stiffness value. An average value of these third and fourth stiffness values obtained in this manner is recorded as the flexural stiffness value in the transverse direction of the core 20 lying in the second area 23.

(4) One of longitudinally opposite end portions of the third sample is held by a chuck of the tester and the other end portion is maintained in engagement with a pendulum of the tester and the tester is initialized by loading an auxiliary weight so that the tester scale may point a reading in a range of 3 to 6; the tester is turned on and a scale reading of the moment at which the pivot rod of the pendulum is separated from the third sample is recorded as a fifth stiffness value. Now the other of longitudinally opposite end portions of the third sample is held by the chuck of the tester and the one of these end portions is maintained in engagement with the pendulum of the tester. The tester is initialized by loading the auxiliary weight so that the tester scale may point a reading in a range of 3 to 6; the tester is turned on and a scale reading of the moment at which the pivot rod of the pendulum is separated from the sample is recorded as a sixth stiffness value. An average value of these fifth and sixth stiffness values obtained in this manner is recorded as the flexural stiffness value in the transverse direction of the core 20 lying in the crotch region 15.

The flexural stiffness value of the first and third samples having been measured in this manner is in a range of 9.4 to 28.2 mN and the flexural stiffness value of the second sample having been measured in this manner is in a range of 5.5 to 16.5 mN. The second sample is formed in its transversely middle zone with the through-hole 25 in which the core 20 is absent and exhibited the flexural stiffness value correspondingly lower than the flexural stiffness value of the first and third samples.

The distal portions 33 of the respective leak-barrier sheets 19 including the elastic members 36 have a stretch stress in a range of 0.02 to 32 N at 90% stretched state. The elastic members 36 are permanently bonded to the distal portions 33 of the leak-barrier sheets 19 and therefore the contractile force of these elastic members 36 is restrained by the stiffness of the distal portions 33. However, the stretch stress of the distal portions 33 in the above-described range allows the contractile force of the elastic members 36 to pull the first area 22 of the rear waist region 16 toward the crotch region 15. If the stretch stress of the distal portions 33 is less than 0.02 N, the contractile force of the elastic members 36 will be too low to pull the first area 22 toward the crotch region 15 and consequently neither the barrier 48 nor the pocket 49 can be formed by the second area 23. If the stretch stress of the distal portions 33 exceeds 0.32 N, the first area 22 may be collapsed toward the crotch region 15 and the pocket 49 formed by the second area 23 may be closed. The stretch stress of the distal portions 33 of the respective leak-barrier sheets 19 was measured by the following method.

(1) The distal portions 33 (inclusive of the elastic members 36) of the leak-barrier sheets 19 were cut out from the article 10A to obtain samples for measurement of the stretch stress having a longitudinal dimension in a range of 200 to 290 mm and a transverse dimension in a range of 10 to 25 mm. For measurement of the stretch stress of the distal portion, the Tensile Tester manufactured by SHIMADZU CORPORATION in Japan was used.

(2) Longitudinally opposite end portions of the sample contracted under the contractile force of the elastic members 36 were clamped by respective chucks of the Tensile Tester(a dimension over which each end portion was clamped by the chuck: about 10 mm, a length dimension of the sample measured between the chucks: about 100 mm). The sample was stretched in the longitudinal direction at a rate of 100 mm/min and, after the sample had been stretched by 90%, the tension was relieved. The sample was stretched again in the longitudinal direction at a rate of 100 mm/min and a force exerted on the Tester at the moment the sample was stretched by 90% was measured as the stretch stress of the free portion of the leak-barrier sheet. The stretch stress of the sample having been measured in this manner was in a range of 0.02 to 0.32 N. As used herein "the sample was stretched by 90%" means that, for example, the sample having its longitudinal dimension of 250 mm was stretched to 250 mm×0.9=225 mm.

Figure 6:
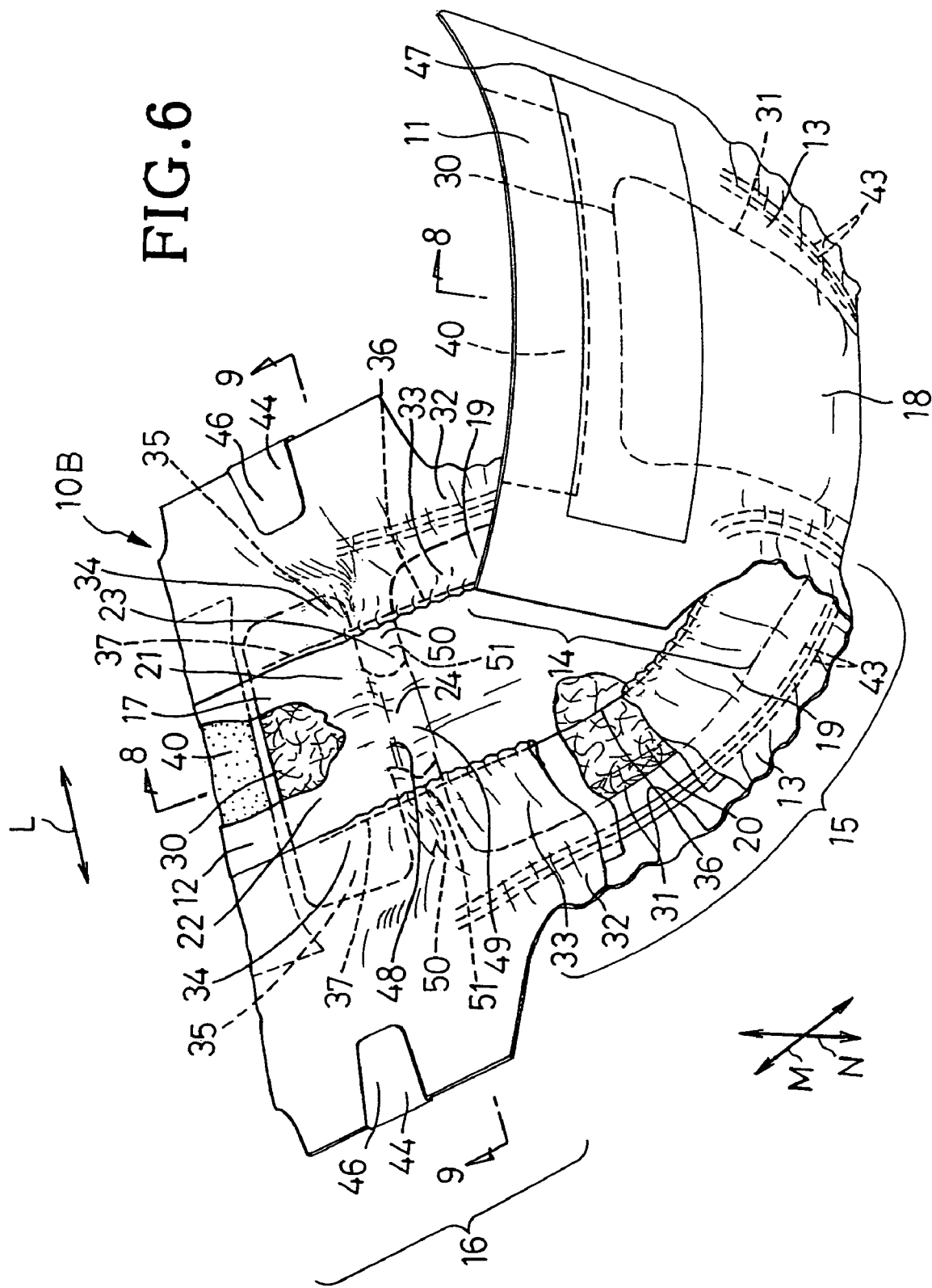
FIG. 6 is a partially cutaway perspective view showing a disposable wearing article as one preferred embodiment of the invention.
Figure 7:
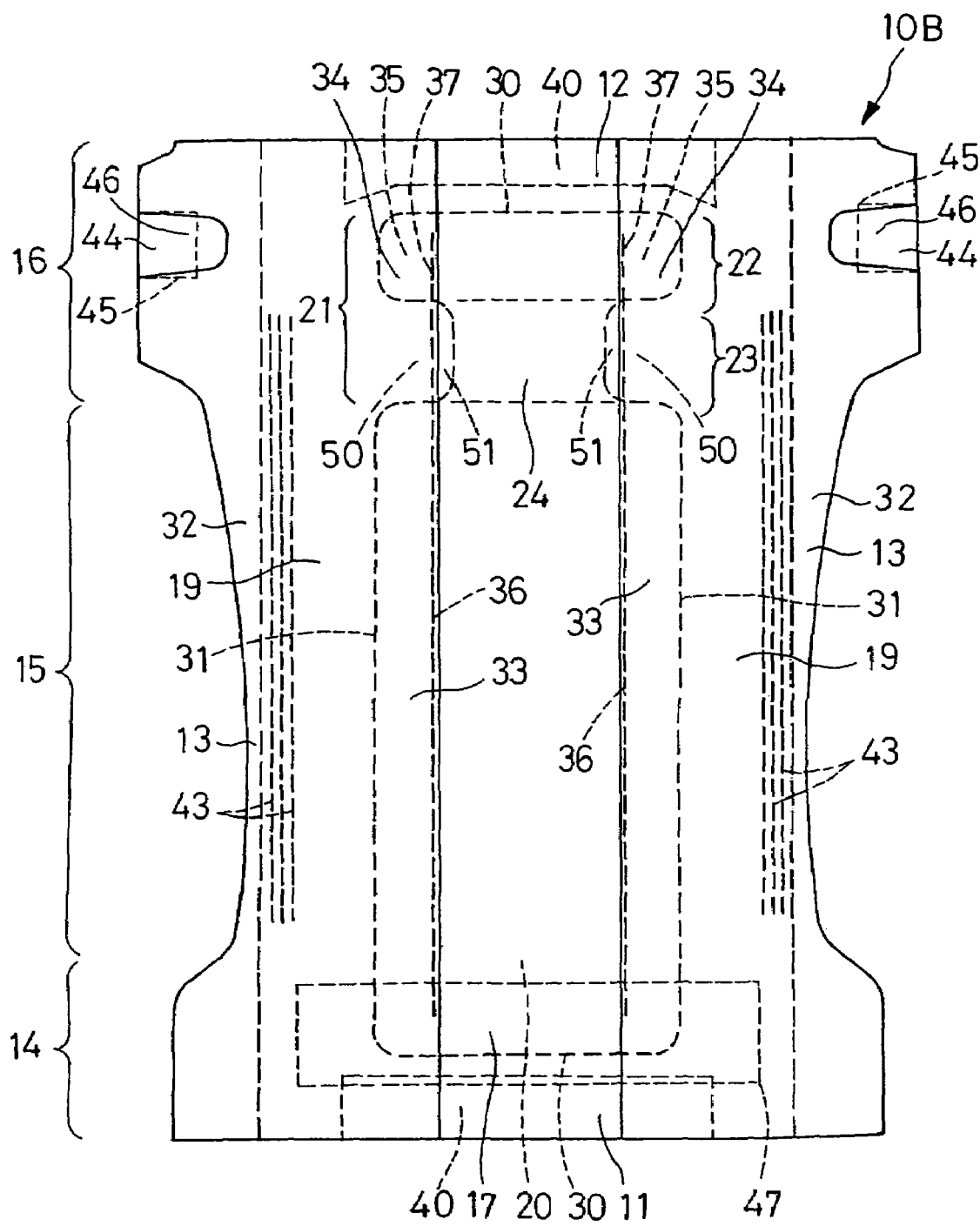
FIG. 7 is a plan view showing the article of FIG. 6 as seen from the side of the topsheet.
Figure 8:
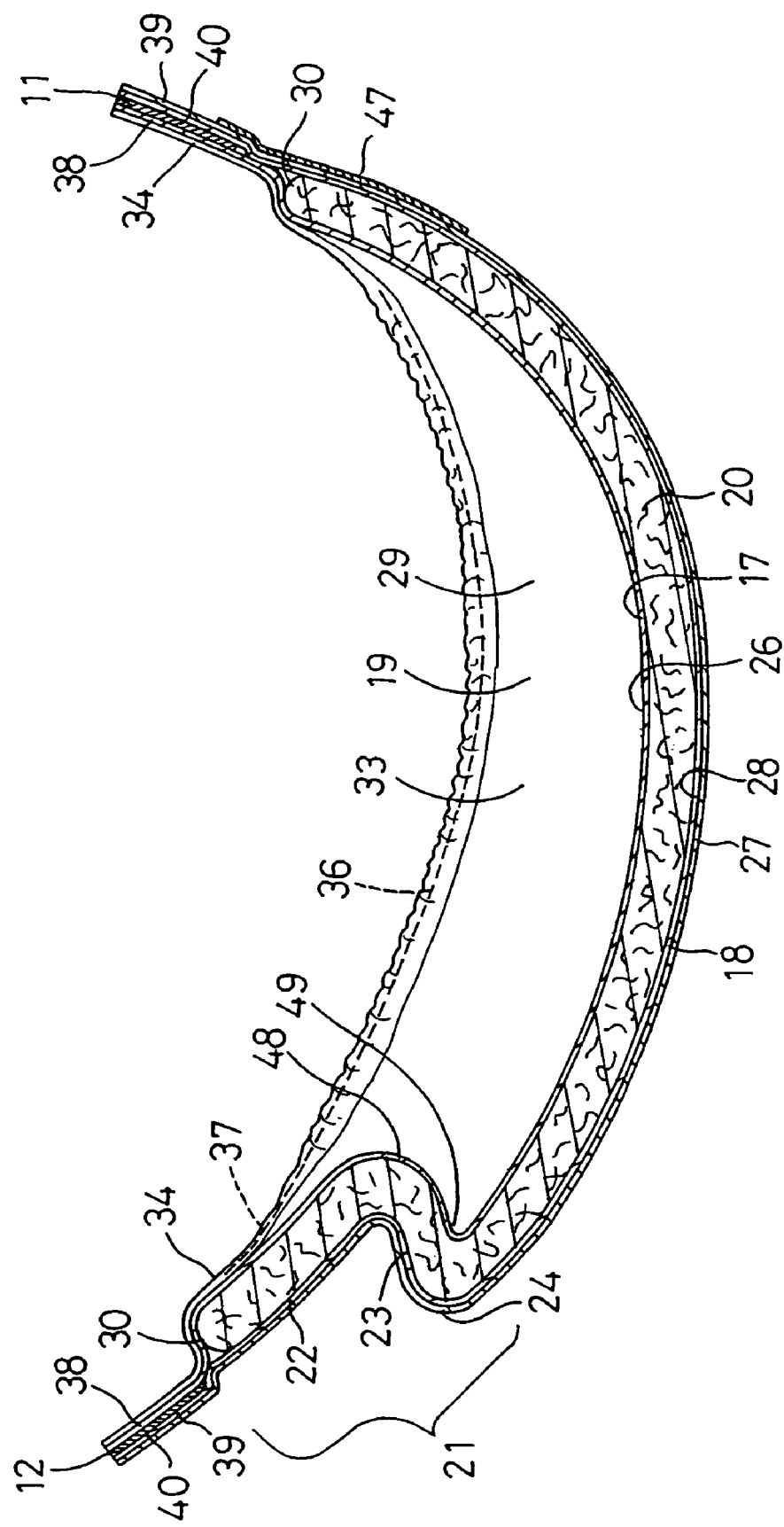
FIG. 8 is a sectional view taken along the line 8-8 in FIG. 6.
Figure 9:
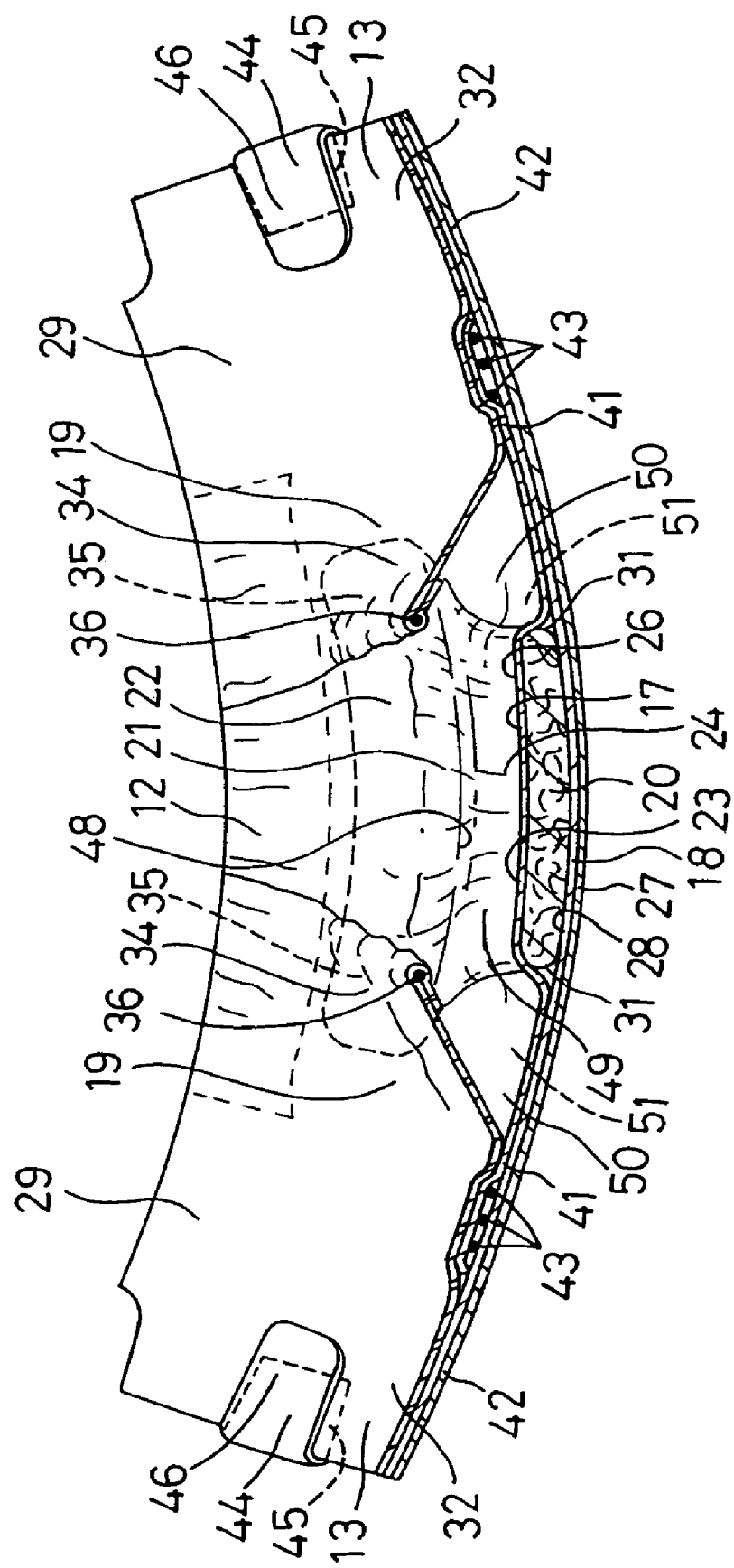
FIG. 9 is a sectional view taken along the line 9-9 in FIG. 6.

FIG. 6 is a partially cutaway perspective view showing a disposable wearing article 10B as one preferred embodiment of the invention, FIG. 7 is a plan view showing the article 10B of FIG. 6 as seen from the side of the topsheet, FIG. 8 is a sectional view taken along the line 8-8 in FIG. 6 and FIG. 9 is a sectional view taken along the line 9-9 in FIG. 6. In FIG. 6, a transverse direction is indicated by an arrow L, a longitudinal direction is indicated by an arrow M and a thickness direction is indicated by an arrow N. In FIG. 7, the article 10B is shown as has been developed in the longitudinal direction as well as in the transverse direction against a contractile force of elastic members 36, 40.

The article 10B is contoured by front and rear end portions 11, 12 extending in parallel to each other in the transverse direction and a pair of side portions 13 extending in the longitudinal direction. Between the front and rear end portions 11, 12, the article 10B has a front waist region 14, a rear waist region 16 and a crotch region 15 extending between these waist regions 14, 16. The article 10B comprises a liquid-previous topsheet 17 facing the wearer's skin, a liquid-impervious backsheet 18 facing away from the wearer's skin, a pair of liquid-impervious leak-barrier sheets 19 lying on the side portions 13 and extending in the longitudinal direction, and a liquid-absorbent core 20 interposed between the top- and backsheets 17, 18 and bonded to respective inner surfaces of these sheets 17, 18. The core 20 extends continuously in the front and rear waist regions 14, 16 and the crotch region 15. In the crotch region 15, the side portions 13 curve inward as viewed in the transverse direction of the article 10B so as to describe circular arcs. The article 10B has a generally hourglass-like planar shape.

An area 21 of the rear waist region 16 in which the core 20 is present is divided into a first area 22 put aside toward the rear end portion 12 and a second area 23 put aside toward the crotch region 15. Along the side zones 50 of the second area 23, the core 20 is partially cut away to form a pair of notches 51 which are concave inward as viewed in the transverse direction. The notches 51 are covered with the top and backsheets 17, 18 having respective inner surfaces permanently bonded to each other.

Similarly to the case shown by the article 1A, the topsheet 17 is formed from a hydrophilic fibrous nonwoven fabric 26 and the backsheet 18 is formed from a composite sheet and the leak-barrier sheets 19 are formed from a hydrophobic fibrous nonwoven fabric 29. The core 20 also comprises the same mixture as that in the article 1A and extends continuously in the front waist region 14, the crotch region 15 and the rear waist region 16. The core 20 is contoured by longitudinally opposite ends extending in the transverse direction and transversely opposite side edges extending in the longitudinal direction.

Basis weight and density as well as thickness dimension of the core 20 are uniform in the crotch region 15 and the first and second areas 22, 23. A transverse dimension of the core 20 lying in the second area 23 (inclusive of the notches 51) is the same as a transverse dimension of the core 20 lying in the crotch region 15 as well as in the first area 22. In spite of the fact that the basis weight and the density as well as the thickness dimension of the core 20 are uniform in the crotch region 15 and the first and second areas 22, 23, the core 20 has a transverse flexural stiffness lower in the second area 23 than in the crotch region 15 and the first area 22. This is because the second area 23 is formed in its transversely side zones 24 with the notches 51 in which the core 20 is absent.

The leak-barrier sheets 19 respectively comprise proximal portions 32 lying on the side portions 13 and extending in the longitudinal direction, distal portions 33 extending in the longitudinal direction along the proximal portions 32 and normally biased to rise up above the topsheet 17, and fixed longitudinally opposite end portions 34 lying on the front and rear end portions 11, 12 and collapsed inward as viewed in the transverse direction of the article 10B. The end portions 34 lying on the side of the rear waist region 16 are respectively laid not only on the rear end portion 12 but also on transversely opposite side portions 35 of the first area 22. Stretchable first elastic members 36 extending in the longitudinal direction are contractibly attached to the distal portions 33 in the vicinity of respective upper ends thereof. The elastic members 36 are stretched at a predetermined ratio in the longitudinal direction and permanently bonded in such a stretched state to the distal portions 33. Longitudinally ends 37 of the elastic members 36 extending into the rear waist region 16 extend beyond the second area 23 to the side portions 35 of the first area 22. The elastic members 36 contract as the article 10B curves in the longitudinal direction with the topsheet 17 inside. Thereupon the distal portions 33 shrink in the longitudinal direction and rise up above the topsheet 17 under a contractile force of the elastic members 36. Thus the distal portions 33 of the leak-barrier sheets 19 form barriers against bodily waste discharged onto the article 10B.

The front and rear end portions 11, 12 comprise respective end portions 38, 39 of the top- and backsheets 17, 18 extending outward in the longitudinal direction beyond the longitudinally opposite ends 30 of the core 20 and the end portions 34 of the respective leak-barrier sheets 19. Along the front and rear end portions 11, 12, the end portions 34, 38, 39 of the sheets 17, 18, 19 are put flat together wherein the respective inner surfaces of the top- and backsheets 17, 18 are permanently bonded to each other and the outer surface of the topsheet 17 is permanently bonded to the inner surfaces of the leak-barrier sheets 19. In the rear waist region 16, the end portions 34 of the leak-barrier sheets 19 have respective inner surfaces thereof are permanently bonded to the outer surface of the topsheet 17 in the vicinity of the side portions 35. Band-like waist-surrounding elastic members 40 extending in the transverse direction outside the longitudinally opposite ends 30 are contractibly attached to the front and rear end portions 11, 12.

The transversely opposite side portions 13 comprise the side portions 41, 42 of the top- and backsheets 17, 18 extending outward in the transverse direction beyond the side edges 31 of the core 20 and the proximal portions 32 of the respective leak-barrier sheets 19. Along the side portions 13, the side portions 41 of the topsheet 17 extend outward in the transversely direction slightly beyond the side edges 31 of the core 20 and the side portions 42 of the backsheet 18 as well as the proximal portions 32 of the leak-barrier sheets 19 extend further outward in the transverse direction beyond the side portions 41 of the topsheet 17. Along the side portions 13, the proximal portions 32, 41, 42 of the sheets 17, 18, 19 are put flat together and the inner surfaces of the top- and backsheets 17, 18 are permanently bonded together and the inner/outer surfaces of the top- and backsheets 17, 18, respectively, and the inner surfaces of the respective leak-barrier sheets 19 are permanently bonded together. A plurality of leg-surrounding elastic members 43 extending in the longitudinal direction are contractibly attached to the side portions 13.

Flexible tape fasteners 44 made of a fibrous nonwoven fabric are respectively attached to the side portions 13 of the rear waist region 16. The proximal end portion 45 is interposed between the side portion 42 of the backsheet 18 and the proximal portion 32 of the leak-barrier sheet 19 and permanently bonded to the respective inner surfaces of these sheets 18, 19. The distal end portion 46 is provided on its inner surface with a hook member (not shown). The target tape strip 47 comprises a plastic film and a loop member (not shown) attached to the film. Procedures for putting the article 10B on the wearer's body is the same as in the case of the article 10A and detailed description thereof is eliminated here.

The second area 23 is partially folded and the first area 22 is pulled toward the crotch region 15 under a contractile force of the elastic members 36 attached to the leak-barrier sheets 19 so that the first area 22 comes above the crotch region in the thickness direction of the article 10B. A difference in level appears between the crotch region 15 and the first area 22 in the thickness direction and the second area 23 forms a pocket 49 defined between a barrier 48 extending in the thickness direction of the article 10B and the crotch region 15. Even if bodily waste discharged on the article put on the wearer's body spreads toward the rear end portion 12, further spreading of bodily waste is prevented by the barrier 48 and it is unlikely that bodily waste might leak out from the article 10B beyond the rear end portion 12. The second area 23 forms a pocket 49 the barrier 48 but also the pocket 49 so that bodily waste flowing toward the rear end portion 12 is received by the pocket 49. In this way, there is no anxiety that bodily waste might leak out beyond the rear end portion 12.

Along the transversely side zones 50 of the second area 23, the core 20 is partially cut away to form a pair of notches 51 which are concave inward as viewed in the transverse direction and a difference in level depending on the thickness dimension of the core 20 appears between the middle zone 24 and the lateral zones 50. With such an arrangement, even when a body weight of the wearer is exerted on the rear waist region 16 and thereby the second area 23 is compressed in the thickness direction of the article 10B, the transversely lateral zones 50 is prevented by the thickness of the core 20 which is present in the transversely middle zone 24 from being collapsed. This is because the transversely middle zone 24 containing the core 20 is folded upon itself before the transversely opposite middle zones 24 of the second area 23 might be folded upon each other. Even if the pocket 49 is collapsed in the transversely middle zone 24 of the second area 23, there is no possibility that the pocket 49 might be collapsed in the transversely opposite side zones 50. Thus the pocket 49 can be kept in the opened state so far as the transversely opposite side zones 50 are concerned, so it is unlikely that bodily waste might leak out from the pocket 49 and further leak out from the article 10B beyond the rear end portion 12 even when a body weight of the wearer's exerted on the rear waist region 16. Bodily waste is reliably absorbed by the core 20 lying in the first area 22 and the transversely middle zone 24 of the second area 23 without staying on the barrier 48 and/or in the pocket 49.

The core 20 lying in the crotch region 15 and the first area 22 has a transverse flexural stiffness in a range of 9.4 to 28.2 mN and the core 20 which is present in the second area 23 has a flexural stiffness in a range of 5.5 to 16.5 mN. If the flexural stiffness of the core 20 lying in the crotch region 15 and the first area 22 is less than 9.4 mN, the contractile force of the elastic members 36 may result in irregular bending of the crotch region 15 and the first area 22. Such irregular bending will make it impossible for the core 20 lying in the crotch region 15 and first area 22 to absorb bodily waste efficiently. If the flexural stiffness of the core 20 lying in the crotch region 15 and first area 22 exceeds 28.2 mN, the flexural stiffness of the crotch region 15 and first area 22 will excessively increase and a feeling of discomfort against the wearer will be correspondingly created. If the flexural stiffness of the core 20 lying in the second area 23 is less than 5.5 mN, the second area 23 may be irregularly bent under the contractile force of the elastic members 36 and it may be impossible for the second area 23 to form the barrier 48 and the pocket 49. If the flexural stiffness of the core 20 lying in the second area 23 exceeds 16.5 mN, it may be difficult for the core 20 lying in the second area 23 to be bent properly and it may be impossible to for the first area 22 to be pulled toward the crotch region 15 under the contractile force of the elastic members 36. Eventually it may be impossible for the second area 23 to form the barrier 48 and the pocket 49.

The flexural stiffness value of the core 20 lying in the crotch region 15 as well as the first and second area 22, 23 was measured by the Gurley Method (in accordance with JIS L 1096-01-8.20.1). This measuring method for the flexural stiffness was the same as in the article 10A. As a sample of the core 20 lying in the second area 23 was the second sample having the core 20 partially cut off to form a pair of notches 51 and its flexural stiffness value was correspondingly lower than the flexural stiffness value of the first and second samples.

In the article 10B, the distal portions 33 of the respective leak-barrier sheets 19 including the elastic members 36 have a stretch stress in a range of 0.02 to 32 N at a 90% stretched state. The elastic members 36 are permanently bonded to the distal portions 33 of the leak-barrier sheets 19 and therefore the contractile force of the elastic members 36 is restrained by the stiffness of the distal portions 33. However, the stretch stress of the distal portions 33 in the above-described range allows the contractile force of the elastic members 36 to pull the first area 22 of the rear waist region 16 toward the crotch region 15. If the stretch stress of the distal portions 33 is less than 0.02 N, the contractile force of the elastic members 36 will be too low to pull the first area 22 toward the crotch region 15 and consequently neither the barrier 48 nor the pocket 49 can be formed by the second area 23. If the stretch stress of the distal portions 33 exceeds 0.32 N, the first area 23 may be collapsed toward the crotch region 15 and the pocket 49 formed by the second area 23 may be closed. The stretch stress of the distal portions 23 of the respective leak-barrier sheets 19 was measured by the following method.

Figure 10:
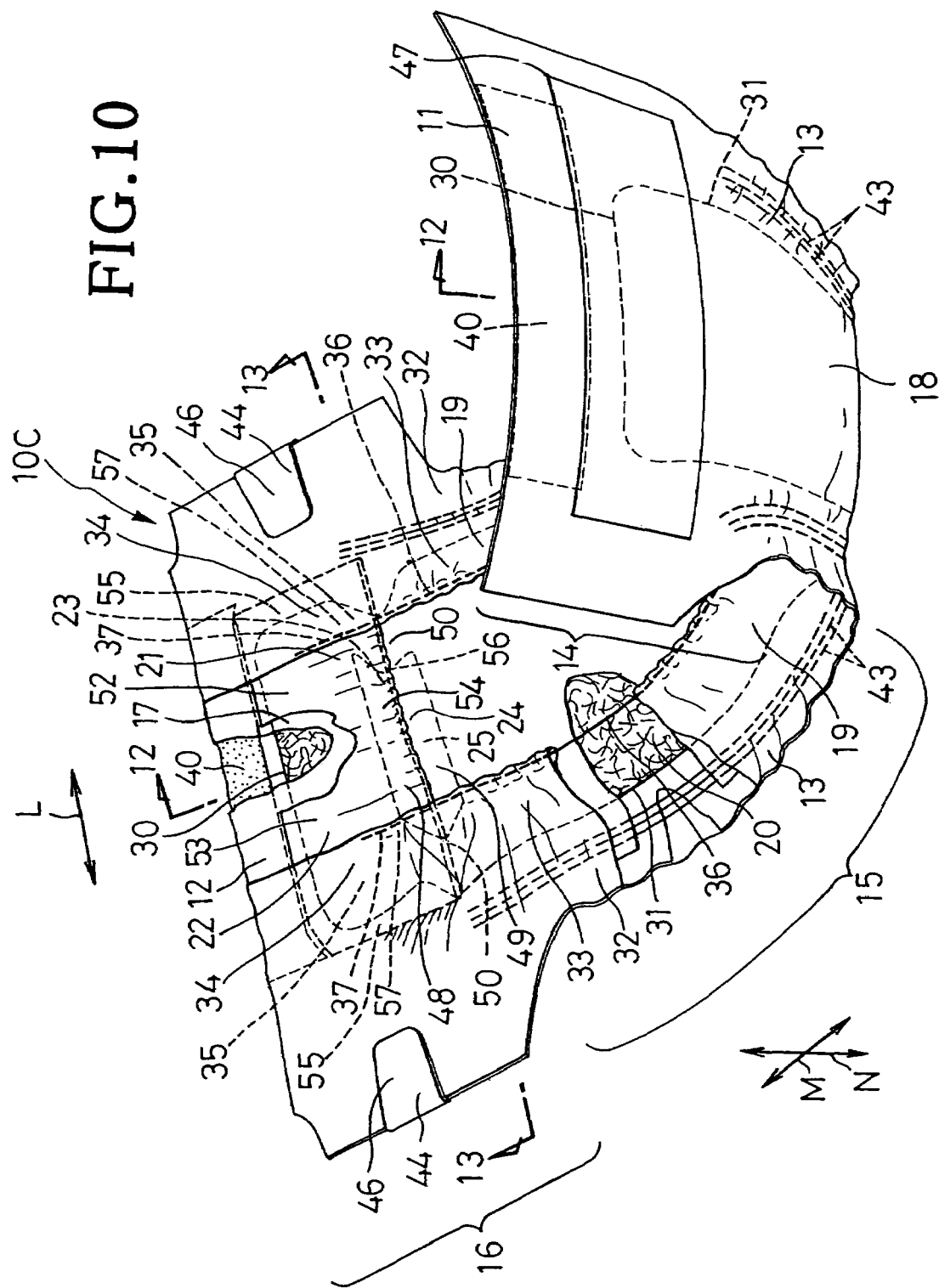
FIG. 10 is a partially cutaway perspective view showing a disposable wearing article as another preferred embodiment of the invention.
Figure 11:
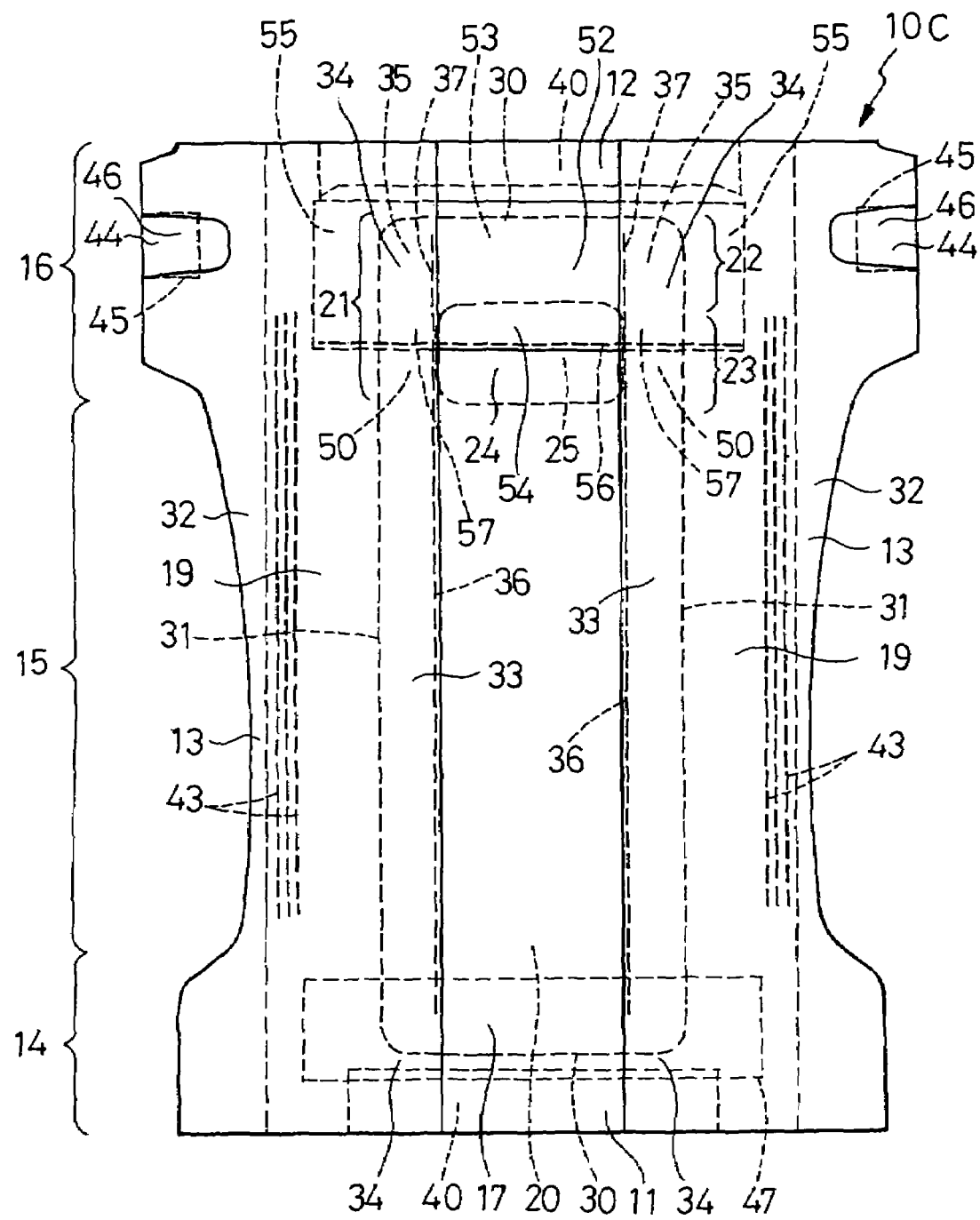
FIG. 11 is a plan view showing the article of FIG. 10 as seen from the side of the topsheet.
Figure 12:
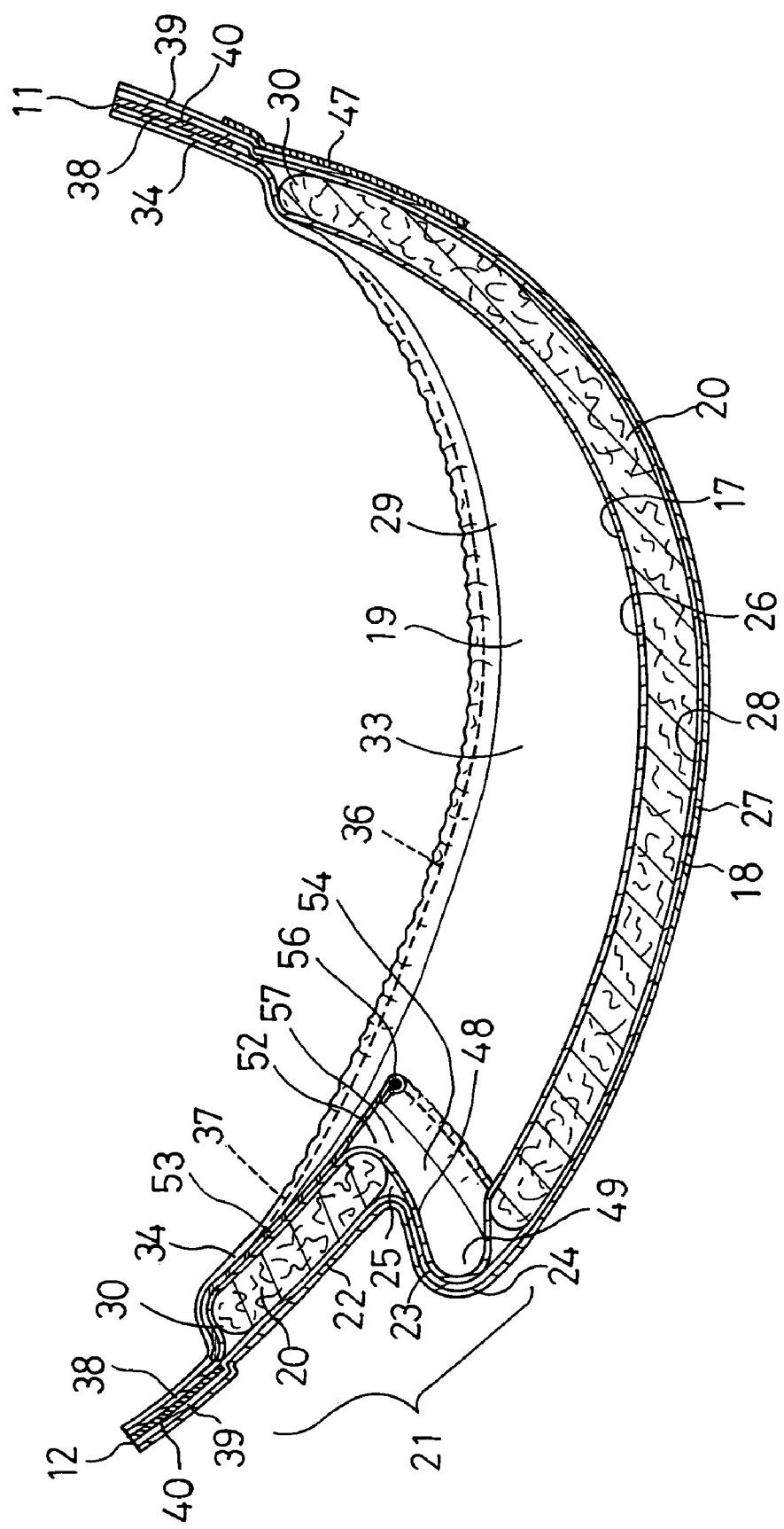
FIG. 12 is a sectional view taken along the line 12-12 in FIG. 10.
Figure 13:
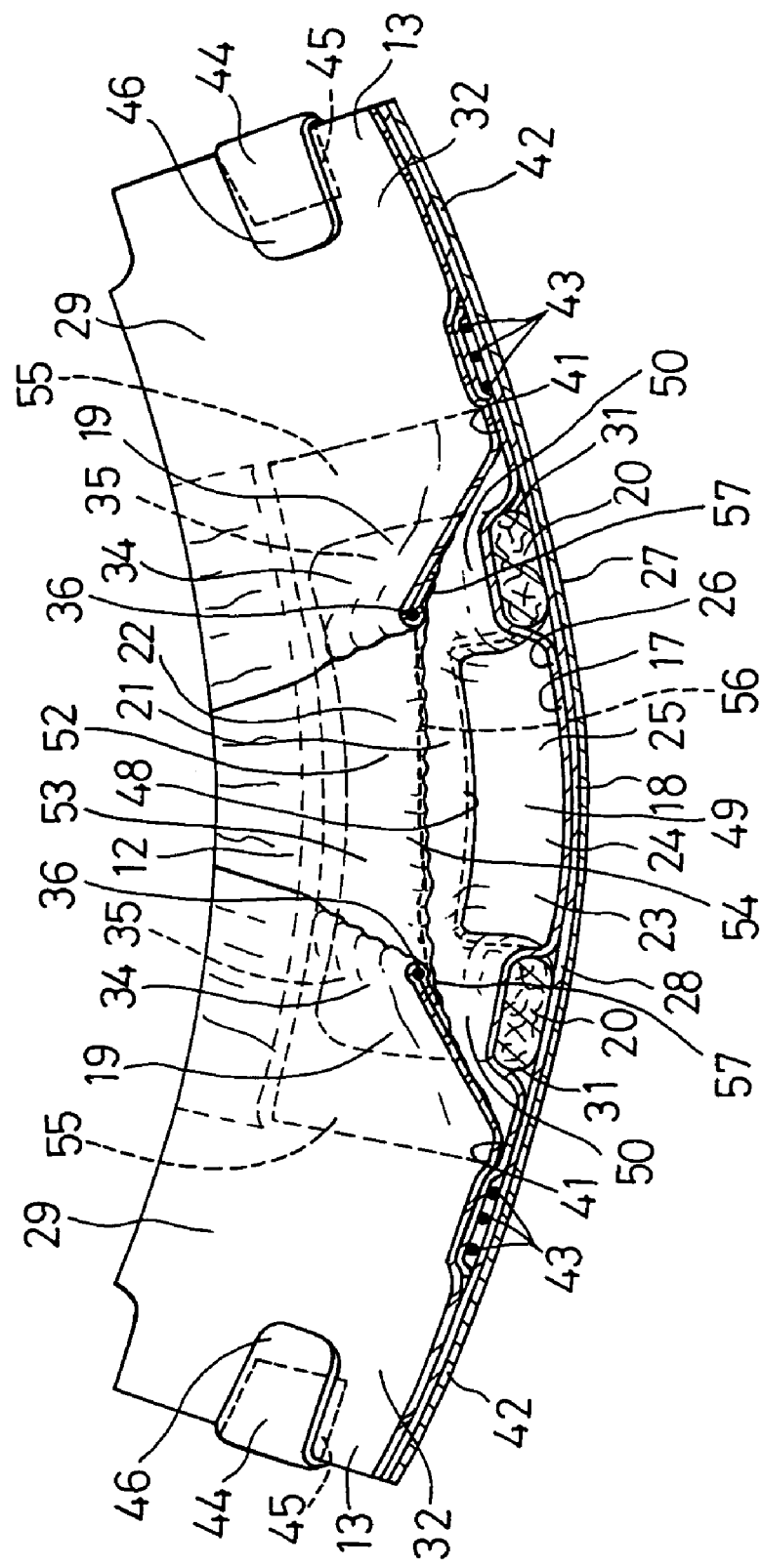
FIG. 13 is a sectional view taken along the line 13-13 in FIG. 10.

FIG. 10 is a partially cutaway perspective view showing a disposable wearing article 10C as another preferred embodiment of the invention, FIG. 11 is a plan view showing the article 10C as seen from the side of the topsheet 17, FIG. 12 is a sectional view taken along the line 12-12 in FIG. 10 and FIG. 13 is a sectional view taken along the line 13-13 in FIG. 10. In FIG. 10, a transverse direction is indicated by an arrow L, a longitudinal direction is indicated by an arrow M and a thickness direction is indicated by an arrow N. FIG. 11 is a plan view showing the article 10C as has been developed in the longitudinal direction as well as in the transverse direction against a contractile force of elastic members 36, 40, 43, 56.

The article 10C is contoured by a pair of longitudinally opposite end portions 11, 12 extending in parallel to each other in the transverse direction and a pair of transversely opposite side portions 13 extending in the longitudinal direction. Between the front and rear end portions 11, 12, the article 10C has a front waist region 14, a rear waist region 16 and a crotch region 15 extending between these waist regions 14, 16. The article 10C comprises a liquid-previous topsheet 17 facing the wearer's skin, a liquid-impervious backsheet 18 facing away from the wearer's skin, a pair of liquid-impervious leak-barrier sheets 19 lying on the side portions 13 and extending in the longitudinal direction, and a liquid-absorbent core 20 interposed between the top- and backsheets 17, 18 and bonded to respective inner surfaces of the sheets 17, 18. The core 20 extends continuously in the front and rear waist regions 14, 16 and the crotch region 15. In the crotch region 15, the side portions 13 curve inward as viewed in the transverse direction of the article 10C so as to describe circular arcs. The article 10C has a generally hourglass-like planar shape.

An area 21 of the rear waist region 16 in which the core 20 is present is divided into a first area 22 put aside toward the rear end portion 12 and a second area 23 put aside toward the crotch region 15. Along the transversely lateral zones 50 of the second area 23, the core 20 is partially cut away to form a pair of notches 51 which are concave inward as viewed in the transverse direction. The notches 51 are covered with the top and backsheets 17, 18 having respective inner surfaces permanently bonded to each other.

Similarly to the case shown by the article 1A, the topsheet 17 is formed by a hydrophilic fibrous nonwoven fabric 26 and the backsheet 18 is formed by a composite sheet and the leak-barrier sheets 19 are formed from a hydrophobic fibrous nonwoven fabric 29. The core 20 also comprises the same mixture as that in the article 1A and extends continuously in the front waist region 14, the crotch region 15 and the rear waist region 16. The core 20 is contoured by longitudinally opposite ends extending in the transverse direction and transversely opposite side edges extending in the longitudinal direction.

Basis weight and density as well as thickness dimension of the core 20 are uniform in the crotch region 15 and the first and second areas 22, 23. A transverse dimension of the core 20 lying in the second area 23 (inclusive of the notches 51) is same as a transverse dimension of the core 20 lying in the crotch region 15 as well as in the first area 22. In spite of the fact that the basis weight and the density as well as the thickness dimension of the core 20 are uniform in the crotch region 15 and the first and second areas 22, 23, the core 20 has a transverse flexural stiffness lower in the second area 23 than in the crotch region 15 and the first region 22. This is because the second area 23 is formed in its transversely lateral zones 24 with the notches 51 in which the core 20 is absent.

The leak-barrier sheets 19 respectively comprise proximal portions 32 lying on the side portions 13 and extending in the longitudinal direction, distal portions 33 extending in the longitudinal direction along the proximal portions 32 and normally biased to rise up above the topsheet 17, and fixed longitudinally opposite end portions 34 lying on the front and rear end portions 11, 12 and collapsed inward as viewed in the transverse direction of the article 10C. The end portions 34 lying on the side of the rear waist region 16 are respectively laid not only on the rear end portion 12 but also on transversely opposite side portions 35 of the first area 22. Stretchable first elastic members 36 extending in the longitudinal direction are contractibly attached to the distal portions 33 in the vicinity of respective upper ends thereof. The elastic members 36 are stretched at a predetermined ratio in the longitudinal direction and permanently bonded in such a stretched state to the distal portions 33. Longitudinally ends 37 of the elastic members 36 extending into the rear waist region 16 extend beyond the second area 23 to the side portions 35 of the first area 22. The elastic members 36 contract as the article 10C curves in the longitudinal direction with the topsheet 17 inside. Thereupon the distal portions 33 shrink in the longitudinal direction and rise up above the topsheet 17 under a contractile force of the elastic members 36. Thus the distal portions 33 of the leak-barrier sheets 19 form barriers against bodily waste discharged onto the article 10C.

A second leak-barrier sheet 52 is laid so as to straddle the first leak-barrier sheets 19. The leak-barrier sheet 52 comprises a proximal portion 53 lying in the first area 22 and extending in the transverse direction, a distal portion 54 extending in the transverse direction from the first area 22 to the second area along the proximal portion 53 and fixed transversely opposite side portions 55 lying on the side portions 13 of the article 10C and collapsed inward as viewed in the longitudinal direction. A stretchable second elastic member 56 extending in the transverse direction is contractibly attached to the distal portion 54 in the vicinity of its upper edge. This elastic member 56 is permanently bonded to the distal portion 54 while the elastic member 56 is stretched in the transverse direction at a predetermined ratio. Transversely opposite lateral zones 57 of the distal portion 54 are permanently bonded to the distal portions 33 of the first leak-barrier sheets 19. The proximal portions 55 are interposed between the end portions 38 of the topsheet 17 and the end portions 34 of the first leak-barrier sheets 19 and the inner/outer surfaces of the respective end portions 34, 38 of the sheets 17, 19. The distal portion 54 of the leak-barrier sheet 52 is spaced apart upward from the topsheet 17 as the distal portions 33 of the leak-barrier sheets 19 rise up above the topsheet 17. Thus the distal portion 54 also forms a barrier adapted to prevent bodily waste from spreading in the longitudinal direction.

The front and rear end portions 11, 12 comprise respective end portions 38, 39 of the top- and backsheets 17, 18 extending outward in the longitudinal direction beyond the longitudinally opposite ends 30 of the core 20 and the end portions 34 of the respective leak-barrier sheets 19. Along the front and rear end portions 11, 12, the end portions 34, 38, 39 of the sheets 17, 18, 19 are put flat together wherein the respective inner surfaces of the top- and backsheets 17, 18 are permanently bonded to each other and the outer surface of the topsheet 17 is permanently bonded to the inner surfaces of the leak-barrier sheets 19. In the rear waist region 16, the end portions 34 of the leak-barrier sheets 19 have respective inner surfaces thereof are permanently bonded to the outer surface of the topsheet 17 in the vicinity of the side portions 35. Band-like waist-surrounding elastic members 40 extending in the transverse direction outside the longitudinally opposite ends 30 are contractibly attached to the front and rear end portions 11, 12.

The side portions 13 comprise the side portions 41, 42 of the top- and backsheets 17, 18 extending outward in the transverse direction beyond the side edges 31 of the core 20 and the proximal portions 32 of the respective leak-barrier sheets 19. Along the side portions 13, the side portions 41 of the topsheet 17 extend outward in the transversely direction slightly beyond the side edges 31 of the core 20 and the side portions 42 of the backsheet 18 as well as the proximal portions 32 of the leak-barrier sheets 19 extend further outward in the transverse direction beyond the side portions 41 of the topsheet 17. Along the side portions 13, the proximal portions 32, 41, 42 of the sheets 17, 18, 19 are put flat together and the inner surfaces of the top- and backsheets 17, 18 are permanently bonded together and the inner/outer surfaces of the top- and backsheets 17, 18, respectively, and the inner surfaces of the respective leak-barrier sheets 19 are permanently bonded together. A plurality of leg-surrounding elastic members 43 extending in the longitudinal direction are contractibly attached to the side portions 13.

Flexible tape fasteners 44 made of a fibrous nonwoven fabric are respectively attached to the side portions 13 of the rear waist region 16. The proximal end portion 45 is interposed between the side portion 42 of the backsheet 18 and the proximal portion 32 of the leak-barrier sheet 19 and permanently bonded to the respective inner surfaces of the sheets 18, 19. The distal end portion 46 is provided on its inner surface with a hook member (not shown). The target tape strip 47 comprises a plastic film and a loop member (not shown) attached to the film. Procedures for putting the article 10C on the wearer's body is the same as in the case of the article 10A and detailed description thereof is eliminated here.

The second area 23 is partially folded and the first area 22 is pulled toward the crotch region 15 under a contractile force of the elastic members 36 attached to the leak-barrier sheets 19 so that the first area 22 comes above the crotch region 15 in the thickness direction of the article 10B. A difference in level appears between the crotch region 15 and the first area 22 in the thickness direction and the second area 23 forms a pocket 49 defined between a barrier 48 extending in the thickness direction of the article 10B and the crotch region 15. Even if bodily waste discharged on the article put on the wearer's body spreads toward the rear end portion 12, further spreading of bodily waste is prevented by the barrier 48 and it is unlikely that bodily waste might leak out from the article 10B beyond the rear end portion 12. The second area 23 forms a pocket 49 the barrier 48 but also the pocket 49 so that bodily waste flowing toward the rear end portion 12 is received by the pocket 49. In this way, there is no anxiety that bodily waste might leak out beyond the rear end portion 12.

Along the transversely side zones 50 of the second area 23, the core 20 is partially cut away to form a pair of notches 51 which are concave inward as viewed in the transverse direction and a difference in level depending on the thickness dimension of the core 20 appears between the middle zone 24 and the lateral zones 50. With such an arrangement, even when a body weight of the wearer is exerted on the rear waist region 16 and thereby the second area 23 is compressed in the thickness direction of the article 10C, the transversely lateral zones 50 is prevented by the thickness of the core 20 which is present in the transversely middle zone 24 50 from being collapsed. This is because the transversely middle zone 24 in which the core 20 is present folded upon itself before the transversely opposite side zones 24 of the second area 23 might be folded upon each other. Even if the pocket 49 is collapsed in the transversely middle zone 24 of the second area 23, there is no possibility that the pocket 49 might be collapsed in the transversely opposite side zones 50. Thus the pocket 49 can be kept in the opened state so far as the transversely opposite side zones 50 are concerned, so it is unlikely that bodily waste might leak out from the pocket 49 and further leak out from the article 10C beyond the rear end portion 12 even when a body weight of the wearer is exerted on the rear waist region 16. Bodily waste is reliably absorbed by the core 20 lying in the first area 22 and the transversely middle zone 24 of the second area 23 without staying on the barrier 48 and/or in the pocket 49.

The distal portion 54 of the second leak-barrier sheet 52 forms a barrier against bodily waste and, even bodily waste discharged on the article 10C put on the wearer's body flows beyond the barriers 48 to the first area 22, such bodily waste is prevented by the distal portion 54 of the leak-barrier sheet 52 from further flowing. The distal portion 54 of the second leak-barrier sheet 52 is permanently bonded along the transversely opposite side portions 57 thereof to the distal portions 33 of the first leak-barrier sheets 19. With such an arrangement, the distal portion 54 is spaced apart upward from the topsheet 17 as the distal portions 33 rise up above the topsheet 17 and therefore the distal portion 54 of the second leak-barrier sheet 52 adequately functions as the barrier adapted to prevent bodily waste from leaking out beyond the rear end portion 12.

The core 20 lying in the crotch region 15 and the first area 22 has a transverse flexural stiffness in a range of 9.4 to 28.2 mN and the core 20 which is present in the second area 23 has a flexural stiffness in a range of 5.5 to 16.5 mN. If the flexural stiffness of the core 20 lying in the crotch region 15 and the first area 22 is less than 9.4 mN, the contractile force of the elastic members 36 may result in irregular bending of the crotch region 15 and the first area 22. Such irregular bending will make it impossible for the core 20 lying in the crotch region 15 and first area 22 to absorb bodily waste efficiently. If the flexural stiffness of the core 20 lying in these crotch region 15 and first area 22 exceeds 28.2 mN, the flexural stiffness of these crotch region 15 and first area 22 will excessively increase and a feeling of discomfort against the wearer will be correspondingly created. If the flexural stiffness of the core 20 lying in the second area 23 is less than 5.5 mN, the second area 23 may be irregularly bent under the contractile force of the elastic members 36 and it may be impossible for the second area 23 to form the barrier 48 and the pocket 49. If the flexural stiffness of the core 20 lying in the second area 23 exceeds 16.5 mN, it may be difficult for the core 20 lying in the second area 23 to be bent properly and it may be impossible for the first area 22 to be pulled toward the crotch region 15 under the contractile force of the elastic members 36. Eventually it may be impossible for the second area 23 to form the barrier 48 and the pocket 49. The flexural stiffness of the core 20 lying in the crotch region 15, the first area 22 and the second area 23 was measured by the Gurley Method (JIS L 1096-01-8.20.1). The method for measuring the flexural stiffness was same as the method used for the article 10A.

The distal portions 33 of the respective leak-barrier sheets 19 including the elastic members 36 have a stretch stress in a range of 0.02 to 32 N at a 90% stretched state. If the stretch stress of the distal portions 33 is less than 0.02 N, the contractile force of the elastic members 36 will be too low to pull the first area 22 toward the crotch region 15 and consequently neither the barrier 48 nor the pocket 49 can be formed by the second area 23. If the stretch stress of the distal portions 33 exceeds 0.32 N, the first area 22 may be collapsed toward the crotch region 15 and the pocket 49 formed by the second area 23 may be closed. The stretch stress of the distal portions 33 of the respective leak-barrier sheets 19 was measured by the same method as the method used for the article 10A.

While the second area 23 forms the barrier 48 extending in the thickness direction of the article 10A, 10B, 10C and the pocket 49 facing the crotch region 15 in the article 10A, 10B, 10C described herein as specific embodiments, it may be contemplated within the scope of the invention that, depending on a stretch stress of the elastic members 36, the second area 23 can form only one of the barrier 48 and the pocket 49. For example, when the first area 22 is insufficiently pulled toward the crotch region 15 under a contractile force of the elastic members 36, the second area 23 tilts toward the rear end portion 12 and formed the barrier 48 alone. When the first area 22 is pulled beyond the second area 23 to the crotch region 15 under a contractile force of the elastic members 36, the second area 23 tilts toward the crotch region 15 and forms the pocket 49 alone.

Stock materials for the topsheet 17 is not limited to the hydrophilic fibrous nonwoven fabric but may be also selected from the group consisting of a hydrophobic fibrous nonwoven fabric having a plurality of perforations and a plastic film having a plurality of fine apertures. Without departing from the scope of the invention, it is possible to form the backsheet 18 using any one selected from the group consisting of a hydrophobic fibrous nonwoven fabric, a breathable liquid-impervious plastic film and a composite nonwoven fabric comprising two or more layers of hydrophobic fibrous nonwoven fabric laminated one upon another. It is possible without departing from the scope of the invention to form the backsheet 18 and the leak-barrier sheets 19, 52 using a composite nonwoven fabric (SM nonwoven fabric, SMS nonwoven fabric or SMMS nonwoven fabric) consisting of a melt blown fibrous nonwoven fabric having a high water-resistance and a spun bond fibrous nonwoven fabric being high in strength as well as in flexibility laminated on at least one side of the melt blown fibrous nonwoven fabric.

Stock materials for the fibrous nonwoven fabric layers may be selected from the group consisting of spun lace-, needle punch-, melt blown-, thermal bond-, spun bond- and chemical bond-nonwoven fabric layers. Component fibers of these nonwoven fabric layers may be selected from the group consisting of polyester-, polyacrylonitril-, polyvinyl chloride-, polyethylene-, polypropylene- and polystyrene-based fibers. It is also possible without departing from the scope of the invention to use the component fibers selected from the group consisting of core-sheath conjugate fibers, side-by-side conjugate fibers, modified macaroni fibers, microporous fibers and fused type conjugate fibers.

Permanently bonding of the top- and backsheets 17, 18 to each other, permanently bonding of the leak-barrier sheets 19, 52 to the sheets 17, 18, bonding of the core 20 to the sheets 17, 18 and permanently bonding of the elastic members 37, 41, 44, 56 to the sheets 17, 18, 19, 52 may be achieved by using adhesive or welding technique such as heat-sealing or sonic sealing. Adhesive may be selected from the group consisting of hot melt adhesive, acrylic adhesive and rubber-based adhesive.

The adhesive is coated on the topsheet 17, the backsheet 18 and the leak-barrier sheets 19, 52 preferably in any one of spiral, wavy, zigzag, dotted or striped pattern. The sheets 17, 18, 19, 52 may be coated with adhesive in such patterns to define adhesive-coated regions and adhesive-free regions in these sheets 17, 18, 19, 52 and thereby to ensure that the sheets 17, 18, 19, 52 are intermittently and permanently bonded one to another, the core 20 is intermittently and permanently bonded to the sheets 17, 18 and the elastic members 37, 41, 44, 56 are intermittently and permanently bonded to the sheets 17, 18, 19, 52.

What is claimed is:
1. A disposable wearing article, comprising:
front and rear end portions extending in a transverse direction of said article and transversely opposite side portions,
said front and rear end portions defining therebetween a front waist region, a rear waist region and a crotch region extending between said waist regions in a longitudinal direction of said article,
a liquid-previous topsheet,
a liquid-impervious backsheet,
a pair of liquid-impervious first leak-barrier sheets laid on said transversely opposite side portions so as to extend in the longitudinal direction, and
a liquid-absorbent core interposed between said topsheet and backsheet so as to extend between said front and rear end portions,
wherein
said first leak-barrier sheets respectively comprise:
proximal portions extending in the longitudinal direction between said front and rear end portions,
distal portions extending in the longitudinal direction along said proximal portions,
fixed longitudinally opposite end portions laid on said front and rear end portions and collapsed in the transverse direction, and
stretchable first elastic members extending in the longitudinal direction and contractibly attached to the distal portions of said first leak-barrier sheets to bias said distal portions to rise up above said topsheet, an area of said rear waist region in which said core extends is divided into a first area lying on a side of said rear end portion and a second area lying on a side of said crotch region,
said second area is formed in a transversely middle zone thereof with a through-hole extending through an entire thickness of said core so that a flexural stiffness of said core is lower in said second area than in said first area,
said proximal portions of said first leak-barrier sheets as well as longitudinal end portions of said first elastic members lie in said first area of said rear waist region; and
a contracting force of the first elastic elements is sufficient to pull the first area toward the crotch region and to a position above the second area and said crotch region, as viewed in a thickness direction of said article, wherein
said first area, said second area and said crotch region define a Z-shape in a cross section taken in said longitudinal direction, and
said second area forms at least one of (a) a barrier extending in the thickness direction of said article and (b) a pocket opening toward said crotch region.

2. The article set forth by claim 1, wherein a basis weight, a density and a thickness dimension of said core are uniform and the same in said crotch region, said first area and said second area, excluding said through-hole.

3. The article set forth by claim 1, further comprising a liquid-impervious second leak-barrier sheet comprising:
a proximal portion lying in the first area of said rear waist region and extending in the transverse direction,
a distal portion extending along said proximal portion in the transverse direction from the first area to the second area of said rear waist region,
fixed transversely opposite side portions lying on a side of the transversely opposite side portions of said article and collapsed inward as viewed in the longitudinal direction, and
a stretchable second elastic member extending in the transverse direction and being contractibly attached to the distal portion of said second leak-barrier sheet.

4. The article set forth by claim 3, wherein
said second leak-barrier sheet extends to straddle the pair of first leak-barrier sheets, and
the distal portion of said second leak-barrier sheet is permanently bonded at opposite end portions thereof to the distal portions of said first leak-barrier sheets, respectively.

5. The article set forth by claim 1, wherein
a transverse flexural stiffness value of said core lying in said crotch region and said first area is in a range of 9.4 to 28.2 mN as measured by Gurley's Method, and
a transverse flexural stiffness value of said core lying in said second area is in a range of 5.5 to 16.5 mN as measured by said Gurley's Method.

6. The article set forth by claim 5, wherein
the distal portions of said first leak-barrier sheets respectively including said first elastic members exhibit a stretch stress in a range of 0.02 to 0.32 N at a 90% stretched state.

7. The article of claim 1, wherein
said second area forms said pocket which includes a cavity defined by said through-hole; and
side walls of said cavity include absorbent material of said core for absorbing body waste received in said cavity.

8. The article of claim 7, wherein
a bottom wall of said cavity is free of the absorbent material of said core, thereby reducing the flexural stiffness of said core in said second area to allow the contracting force of the first elastic elements to pull the first area toward the crotch region and to the position above the second area.

9. The article of claim 8, wherein a density and a thickness dimension of the absorbent material of said core are uniform throughout said crotch region, said first area and said second area, excluding said bottom wall of said cavity.

10. A disposable wearing article, comprising:
a front waist region, a rear waist region and a crotch region extending between said waist regions in a longitudinal direction of said article;
a liquid-previous topsheet, a liquid-impervious backsheet, and a liquid-absorbent core interposed between said topsheet and backsheet and comprising an absorbent material;
said front waist region, rear waist region and crotch region having portions that are located outside a boundary of said core and define front and rear end portions as well as transversely opposite side portions of said article; and
a pair of longitudinally extending liquid-impervious leak-barrier sheets laid on said transversely opposite side portions, respectively;
wherein
each said first leak-barrier sheet comprises:
a proximal portion extending in the longitudinal direction between said front and rear end portions and being bonded to the respective one of said transversely opposite side portions of said article,
distal portion extending in the longitudinal direction along said proximal portion,
longitudinally opposite end portions extending in a transverse direction of said article between said proximal and distal portions and being bonded to said front and rear end portions, respectively, and
a stretchable first elastic member extending in the longitudinal direction and being contractibly attached to the distal portion to bias said distal portion to rise upwardly above said topsheet;
an area of said rear waist region in which said core extends comprises a first area adjacent the rear end portion and a second area adjacent the crotch region;

said second area is formed in a transversely middle zone thereof with a through-hole extending through an entire thickness of said core so that a flexural stiffness of said core is lower in said second area than in said first area;

said end portions of said first leak-barrier sheets are located in said first area and bonded to portions of the topsheet which cover the core in said first area;

a contracting force of the first elastic elements is sufficient to pull the first area toward the crotch region and to an elevation above said second area and the crotch region, as viewed in a thickness direction of said article, wherein said first area, said second area and said crotch region define a Z-shape in a cross section taken in said longitudinal direction; and said second area defines a folding guide line along which said core and said rear waist region are folded under the action of the contracting force of the first elastic elements to form a pocket opening toward said crotch region.

11. The article of claim 10, wherein the absorbent material of said core is present in side walls of a cavity defined by said through hole for absorbing body waste received therein; and said cavity further comprises a bottom wall free of the absorbent material of said core, thereby reducing the flexural stiffness of said core in said second area to allow the contracting force of the first elastic elements to pull the first area toward the crotch region and to the elevation above the second area and the crotch region.

12. The article of claim 11, wherein a thickness dimension of the absorbent material of said core are uniform in said crotch region, said first area and said second area, excluding said bottom.

13. The article set forth by claim 11, wherein said bottom wall includes a section of said topsheet and a corresponding section of said backsheet underlying said section of said topsheet with no said absorbent material between said sections of the topsheet and backsheet.

14. The article set forth by claim 13, wherein the distal portions of said first leak-barrier sheets respectively including said first elastic members exhibit a stretch stress in a range of 0.02 to 0.32 N at a 90% stretched state.

15. The article set forth by claim 14, wherein a transverse flexural stiffness value of said core lying in said crotch region and said first area is in a range of 9.4 to 28.2 mN as measured by Gurley's Method, and a transverse flexural stiffness value of said core lying in said second area is in a range of 5.5 to 16.5 mN as measured by said Gurley's Method.

16. The article set forth by claim 11, further comprising a liquid-impervious second leak-barrier sheet elongated in the transverse direction and covering said pocket from above.

* * * * *